(12) United States Patent
Abe et al.

(10) Patent No.: US 7,859,680 B2
(45) Date of Patent: Dec. 28, 2010

(54) OPTICAL IMAGE MEASUREMENT DEVICE

(75) Inventors: Tomoyoshi Abe, Tokyo (JP); Takefumi Hayashi, Tokyo (JP); Hiroaki Okada, Tokyo (JP)

(73) Assignee: Kabushiki Kaisha Topcon, Itabashi-Ku (JP)

( * ) Notice: Subject to any disclaimer, the term of this patent is extended or adjusted under 35 U.S.C. 154(b) by 60 days.

(21) Appl. No.: 12/011,768

(22) Filed: Jan. 29, 2008

(65) Prior Publication Data

US 2009/0027685 A1    Jan. 29, 2009

(30) Foreign Application Priority Data

Jan. 26, 2007    (JP)    ............... 2007-017151
Dec. 25, 2007    (JP)    ............... 2007-332091

(51) Int. Cl.
*G01B 9/02* (2006.01)

(52) U.S. Cl. .................................................. 356/479

(58) Field of Classification Search ............... 356/497, 356/479; 385/88, 90
See application file for complete search history.

(56) References Cited

U.S. PATENT DOCUMENTS

| | | | |
|---|---|---|---|
| 6,069,698 A * | 5/2000 | Ozawa et al. | ............... 356/511 |
| 6,377,349 B1 * | 4/2002 | Fercher | ....................... 356/497 |
| 6,616,346 B1 | 9/2003 | Brown et al. | |
| 2006/0164639 A1 | 7/2006 | Horn et al. | |
| 2007/0188765 A1 * | 8/2007 | Zhao et al. | ................... 356/479 |
| 2007/0222945 A1 * | 9/2007 | Tsukada et al. | ............. 351/205 |

FOREIGN PATENT DOCUMENTS

| | | |
|---|---|---|
| DE | 4309056 | 9/1994 |
| JP | 11-325849 | 11/1999 |
| JP | 2003-000543 | 1/2003 |
| WO | WO-2006/021929 | 3/2006 |
| WO | WO-2006/039091 | 4/2006 |
| WO | WO-2007/084750 | 7/2007 |

OTHER PUBLICATIONS

European Search Report dated May 20, 2008, issued on the corresponding European patent application No. 08001367.5.

* cited by examiner

*Primary Examiner*—Tarifur Chowdhury
*Assistant Examiner*—Jonathon D Cook
(74) *Attorney, Agent, or Firm*—Edwards Angell Palmer & Dodge LLP

(57) ABSTRACT

An optical image measuring device forms an image of an object to be measured based on a result of light-receiving by a light-receiving part. This optical image measuring device comprises: a specifying part configured to specify the light irradiated state to the light-receiving surface of a light-receiving part via a light guiding part and a dispersion part; and an altering part configured to alter the relative position and/or direction between a light-receiving surface and the exit end of light from the light guiding part, based on the light irradiated state.

13 Claims, 17 Drawing Sheets

OPTICAL IMAGE MEASUREMENT DEVICE

BACKGROUND OF THE INVENTION

1. Field of the Invention

The present invention relates to an optical image measurement device configured to apply a low coherence light beam to a measurement object and form an image of the surface morphology or internal morphology of the measurement object by using a reflected light or a transmitted light.

2. Description of the Related Art

In recent years, attention has been focused on an optical image measurement technology of forming an image showing the surface morphology or internal morphology of a measurement object by using a light beam from a laser light source or the like. Because this optical image measurement technology does not have invasiveness to human bodies unlike an X-ray CT device, it is particularly expected to further use this technology in the medical field.

Japanese Unexamined Patent Application Publication JP-A 11-325849 discloses an optical image measurement device having a configuration that: a measuring arm scans an object through a rotary deflection mirror (Galvano mirror); a reference mirror is disposed to a reference arm; an interferometer is used at the outlet so that the intensity of light appearing from interference of light fluxes from the measuring arm and the reference arm is analyzed by a spectrometer; and a device gradually changing the light flux phase of the reference light in non-continuous values is disposed to the reference arm.

The optical image measurement device of JP-A 11-325849 uses a method of so-called "Fourier Domain Optical Coherence Tomography (OCT)" based on technology of German Patent Application Publication DE4309056A1. In other words, it is image creation of a morphology of an object to be measured depthwise by the following steps: irradiating the object to be measured with a low-coherence light beam; dispersing (spectral resolving) an interference light that is based on the reflected light thereof; detecting the spectral intensity distribution thereof with a light detector such as a CCD; and carrying out Fourier transformation of the detection results. Herein, the interference light generated from a signal light and a reference light is adapted to be guided by an optical fiber (light guiding part) to exit from a fiber end, spectrally resolved with a diffraction grating or the like, and detected by the light detector.

Furthermore, the optical image measurement device described in JP-A 11-325849 is provided with a Galvano mirror that scans with an optical beam (signal light), whereby it is possible to form an image of a desired measurement region of a measurement object. Because this optical image measurement device is configured to scan with a light beam only in one direction orthogonal to the depth-direction, a formed image is a 2-dimensional cross-sectional image of the depth direction along the light beam scanning direction.

Besides, Japanese Unexamined Patent Application Publication JP-A 2003-543 discloses a configuration in which the aforementioned optical image measurement device is applied to the field of opthalmology.

For such an optical image measuring device, the positional relationship between the position of the fiber end of the optical fiber that guides the interference light and the light detector that detects the interference light that has been spectrally resolved is important. In other words, when intervened by a misalignment in the positional relationship between them, the interference light that has been spectrally resolved is no longer properly irradiated on the light-receiving surface of the light detector, so it may not be capable of properly forming an image because the light detector cannot receive the interference light or the amount of light received by the light detector becomes insufficient.

For traditional optical image measuring devices, when the positional relationship between the fiber end and the light-receiving surface of the light detector is disturbed, the user manually adjusts the position of the fiber end or the position of the light detector, or a serviceman from a maintenance service company is called out to adjust the position.

In this way, for traditional optical image measuring devices, there is a problem in that the alignment between the fiber end and the light-receiving surface has to be carried out, requiring substantial labor or time.

In addition, the suitability of the positional relationship between the fiber end and the light-receiving surface is revealed only after a measurement has actually been conducted, so it may not be capable of obtaining an image at the timing when the user desires.

Moreover, because the fiber end surface is minute (i.e. a diameter of only approximately a few μm) the alignment between the fiber end and the light-receiving surface of the light detector needs to be carried out very precisely. In addition, a line sensor is often used as the light detector, but the width of the line sensor is typically approximately from a few μm to less than 20 μm, so it is required that the alignment be carried out particularly precisely widthwise. Meanwhile, the positional relationship between the fiber end and the light-receiving surface is easily altered by a shock to the device housing, environmental conditions such as temperature or humidity, or the like. Therefore, for traditional optical image measuring devices, precise alignment between the fiber end and the light-receiving surface has to be conducted at a considerable frequency.

SUMMARY OF THE INVENTION

The present invention is intended to resolve the problems as described above, and the objective thereof is to provide an optical image measuring device that is capable of easily adjusting the positional relationship between the exit position of the interference light from the light guiding part and the light-receiving surface that receives the interference light.

In an aspect of the present invention, an optical image measuring device comprises: a light source configured to output low-coherence light; an interference light generation part configured to generate the interference light by separating said low-coherence light into a signal light and a reference light and superimposing the signal light via the object to be measured on said reference light; a light guiding part configured to guide said interference light; a dispersion part configured to disperse said guided interference light; and a light-receiving part configured to receive said dispersed interference light, wherein an image of the object to be measured is formed based on the result of light-receiving by said light-receiving part, said optical image measuring device comprising: a specifying part configured to specify the light irradiated state to the light-receiving surface of said light-receiving part via said light guiding part and said dispersion part; and an altering part configured to alter the relative position and/or direction between said light-receiving surface and the exit end of said light from said light guiding part, based on the light irradiated state.

With such an optical image measuring device, it is possible to automatically alter, based on irradiation state of light onto the light-receiving surface, the positional relationship between the exit end of the light guiding part from which interference light exits and the light-receiving surface of the light-receiving part that receives the interference light, thereby making it possible to easily carry out adjustment of the positional relationship between them.

DETAILED DESCRIPTION OF THE PREFERRED EMBODIMENT

Figure 1:
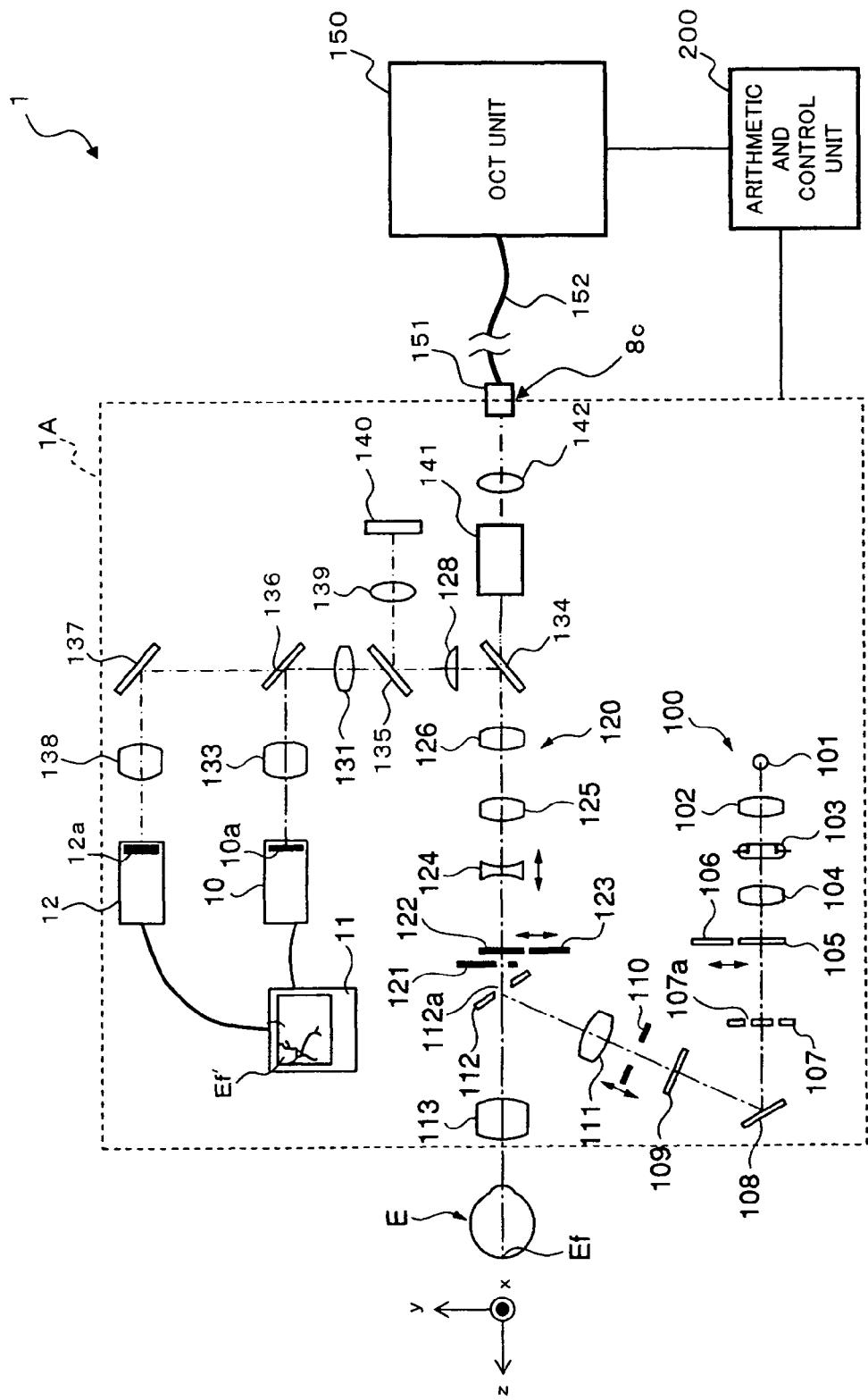
FIG. 1 is a schematic configuration diagram showing one example of the entire configuration in a preferred embodiment of a device related to the present invention.

One example of a preferred embodiment of an optical image measurement device according to the present invention will be described in detail referring to the drawings.

[Configuration of Device]

Figure 2:
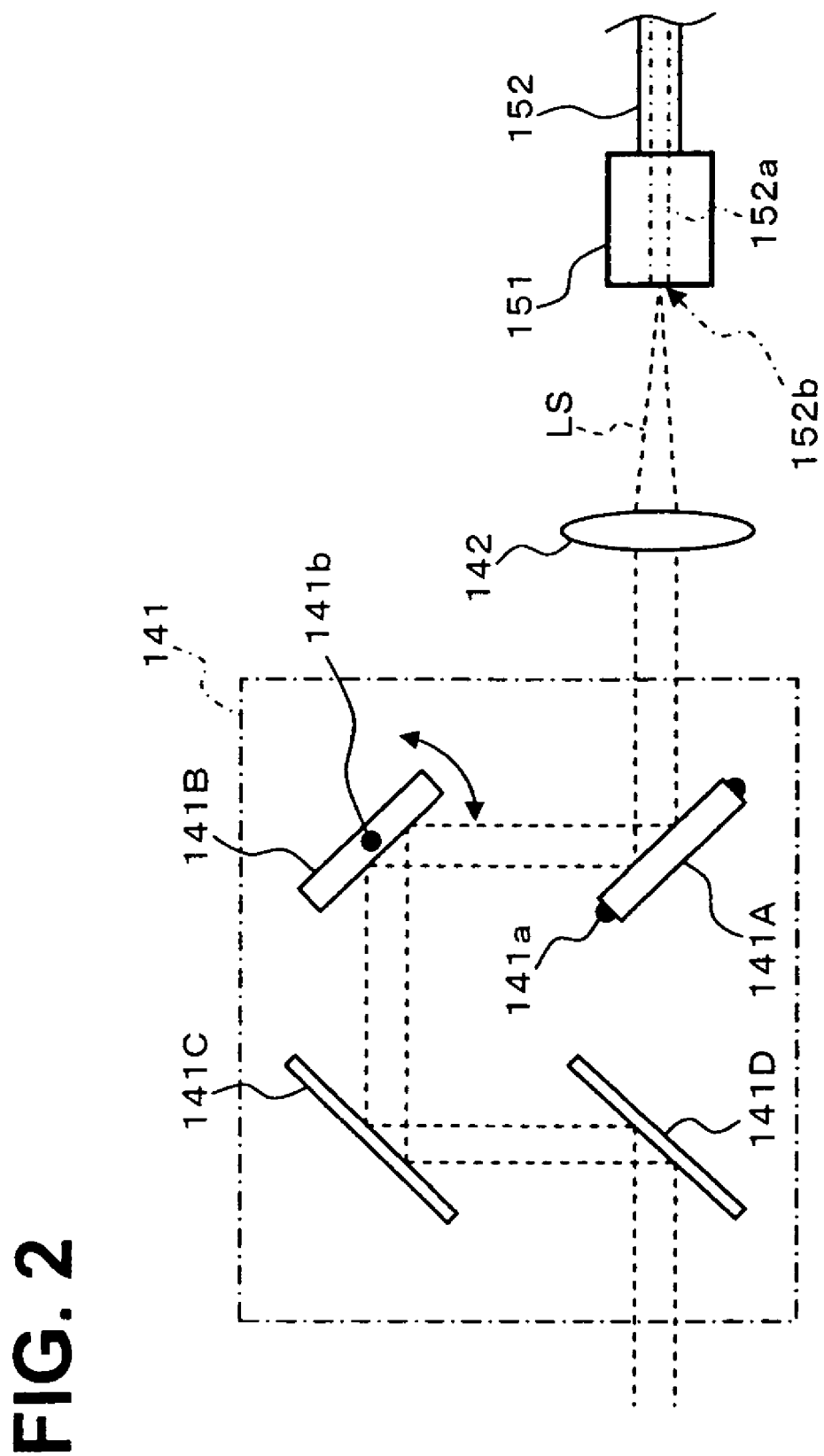
FIG. 2 is a schematic configuration diagram showing one example of the configuration of a scan unit installed in a retinal camera unit in the preferred embodiment of the device related to the present invention.
Figure 3:
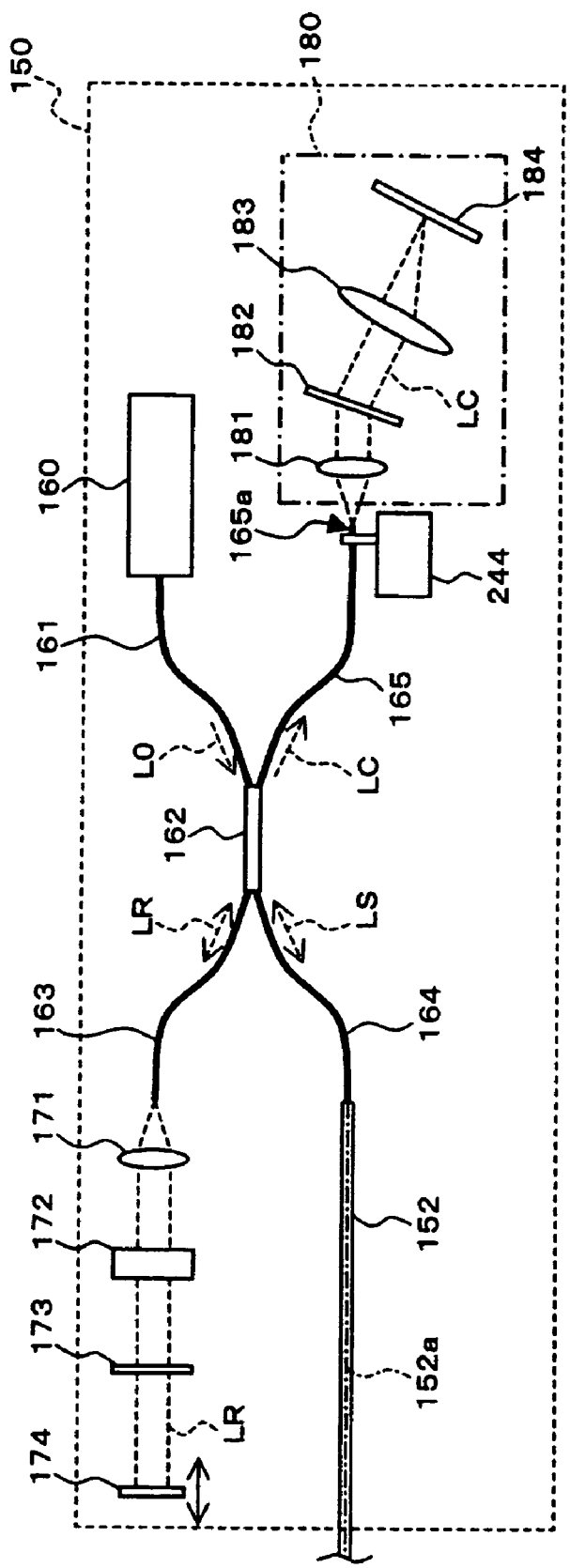
FIG. 3 is a schematic configuration diagram showing one example of the configuration of an OCT unit in the preferred embodiment of the device related to the present invention.
Figure 4:
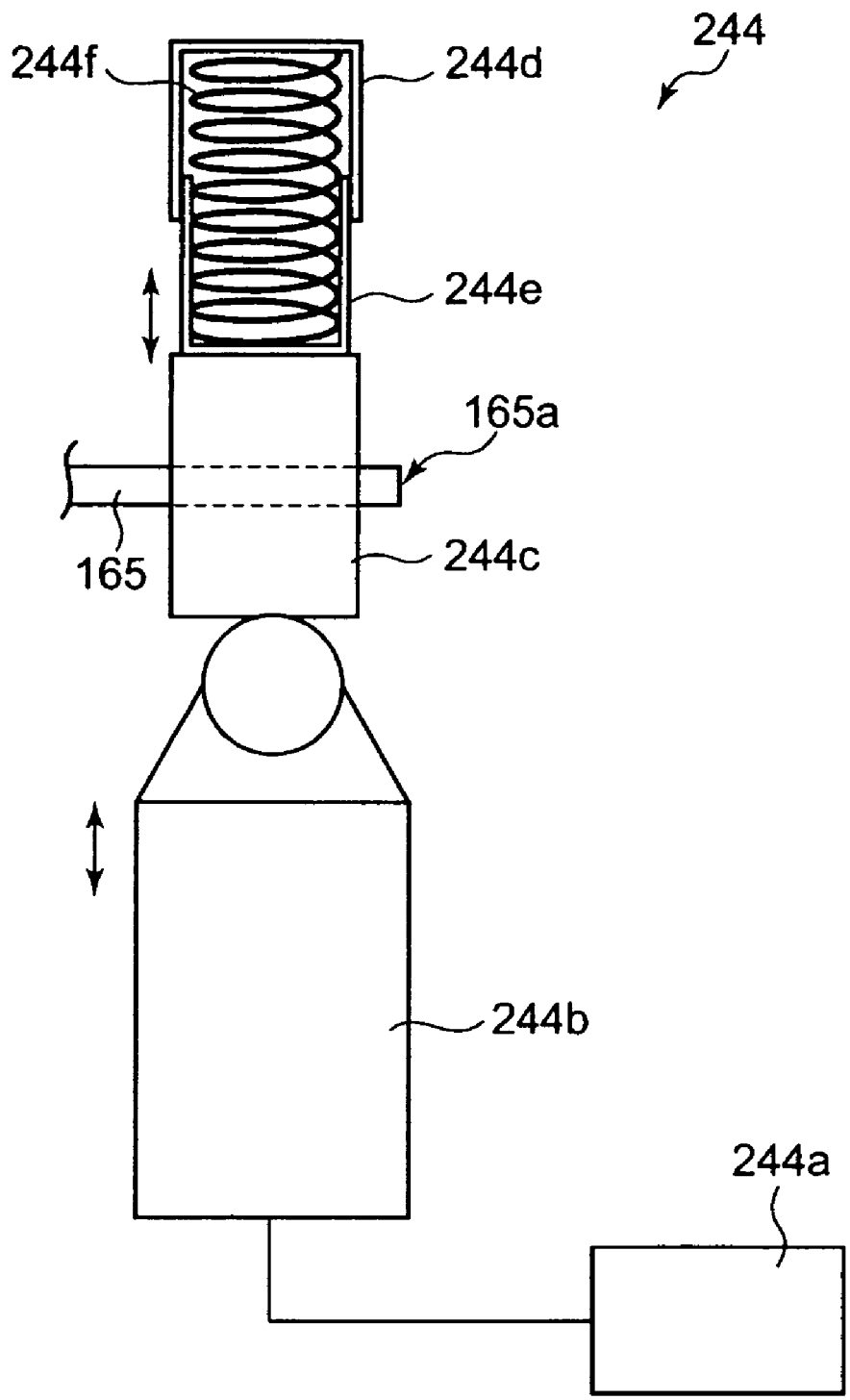
FIG. 4 is a schematic configuration diagram showing one example of the configuration of fiber end driving mechanism in the preferred embodiment of the device related to the present invention.
Figure 5:
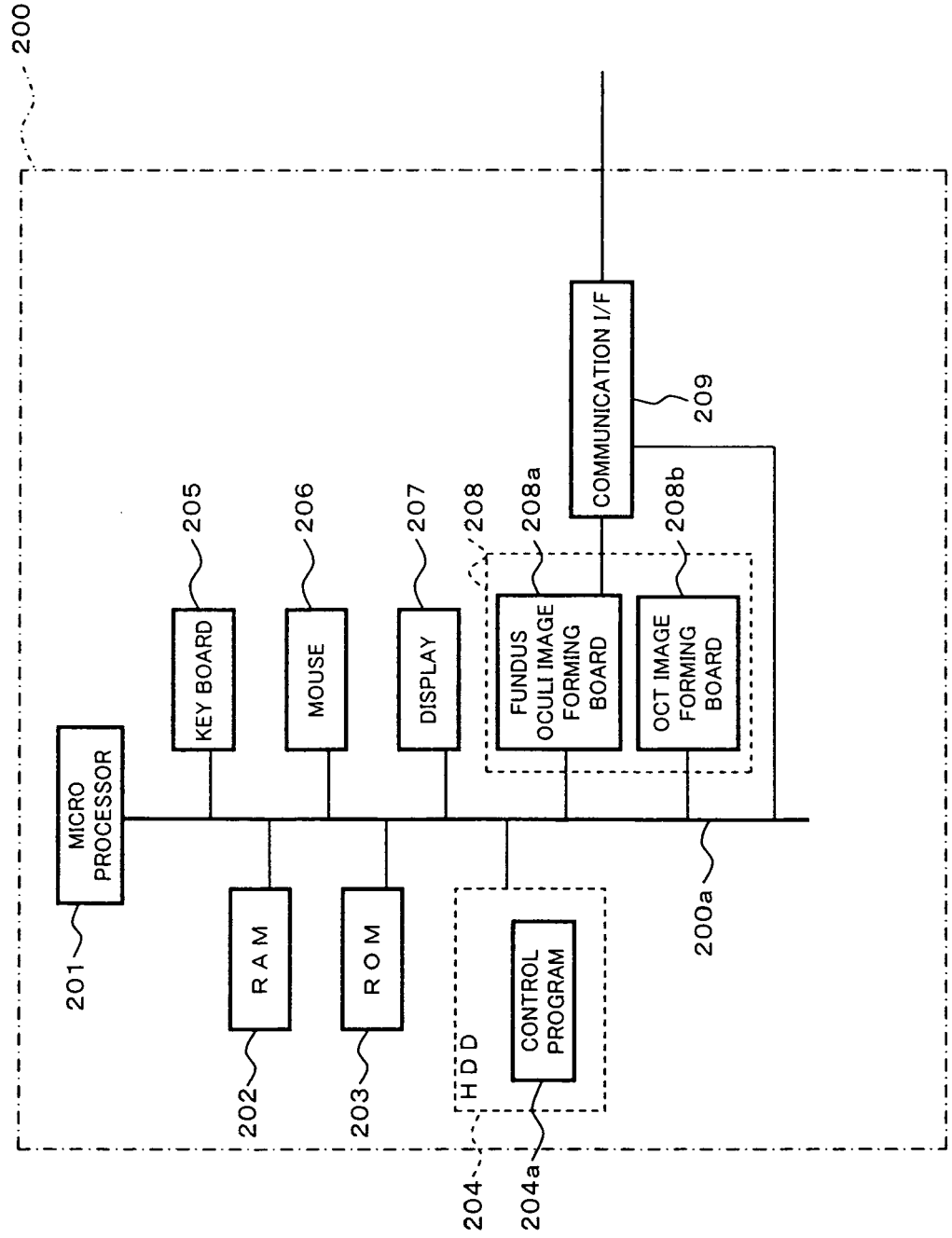
FIG. 5 is a schematic block diagram showing one example of the hardware configuration of an arithmetic control unit in the preferred embodiment of the device related to the present invention.
Figure 6:
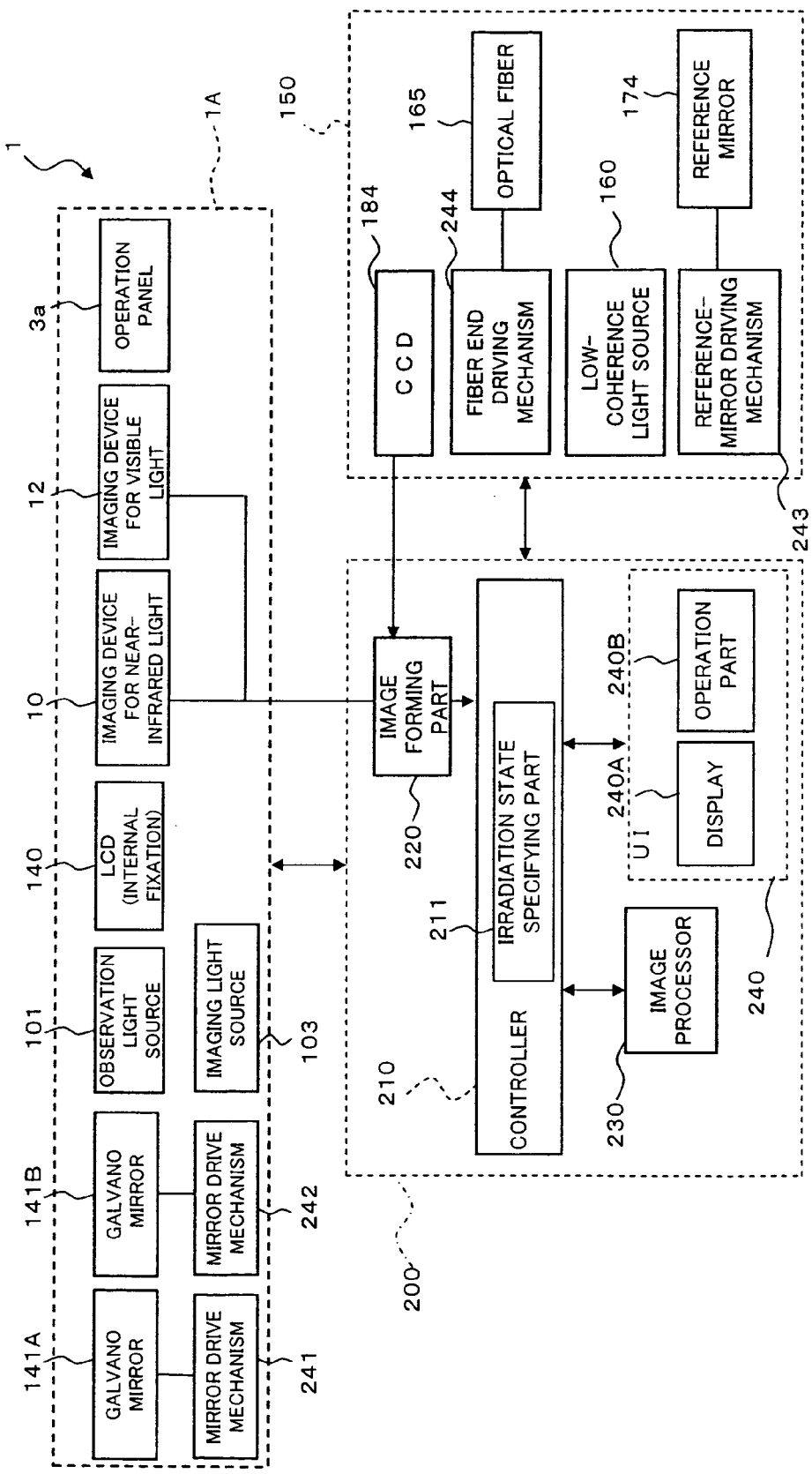
FIG. 6 is a schematic block diagram showing one example of the configuration of a control system in the preferred embodiment of the device related to the present invention.
Figure 7:
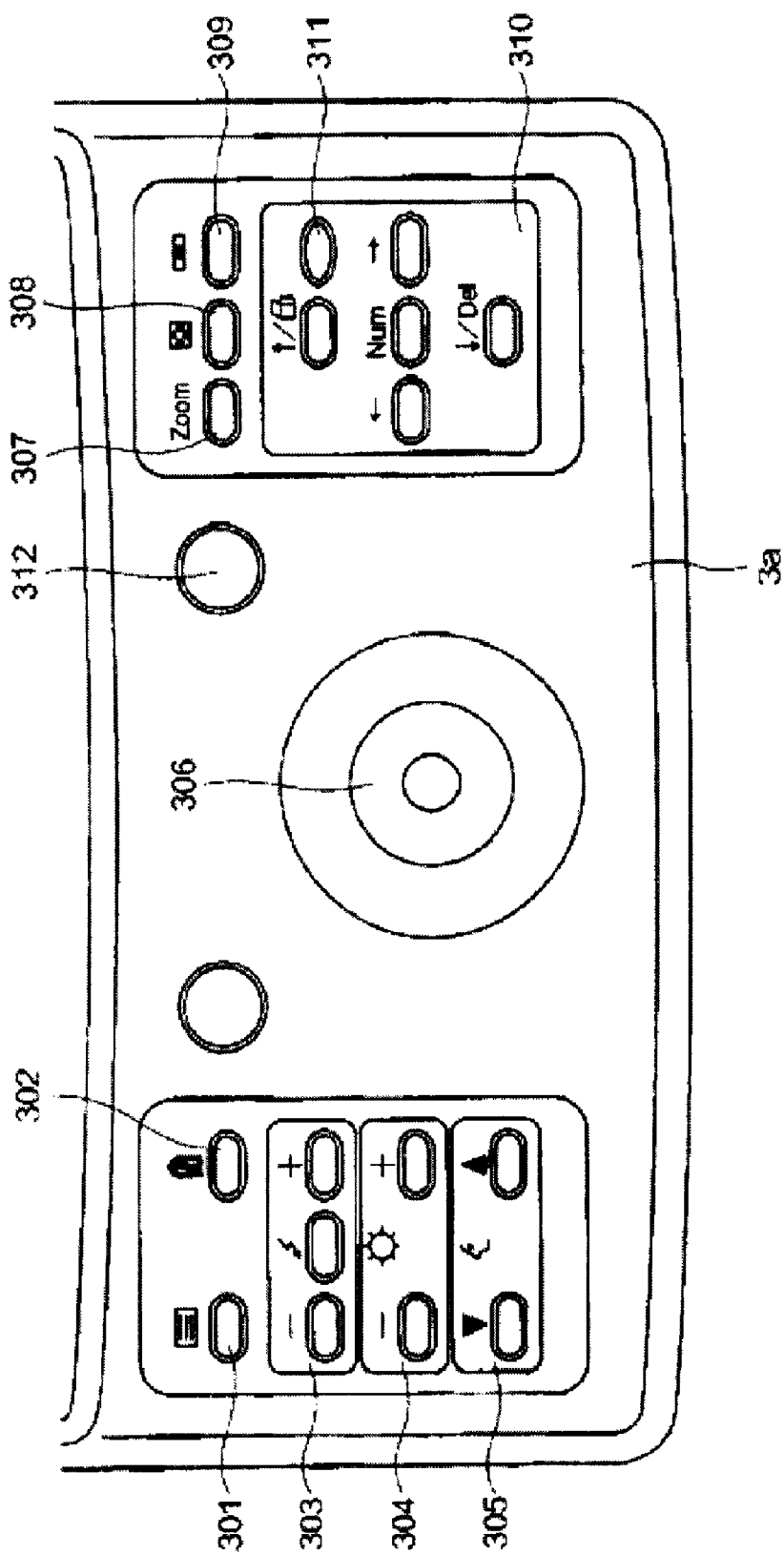
FIG. 7 is a schematic view showing one example of the appearance of an operation panel in the preferred embodiment of the device related to the present invention.

First, referring to FIGS. 1 through 7, the configuration of the optical image measurement device according to an embodiment of the present invention will be described. FIG. 1 shows one example of the entire configuration of a fundus oculi observation device 1 having a function as the optical image measurement device according to this embodiment. FIG. 2 shows one example of the configuration of a scan unit 141 in a retinal camera unit 1A. FIG. 3 shows one example of the configuration of an OCT unit 150. FIG. 4 shows one example of the construction of a fiber end driving mechanism. FIG. 5 shows one example of the hardware configuration of an arithmetic control unit 200. FIG. 6 shows one example of the configuration of a control system of the fundus oculi observation device 1. FIG. 7 shows one example of the configuration of an operation panel 3a disposed to the retinal camera unit 1A.

[Entire Configuration]

The fundus oculi observation device 1 related to this embodiment comprises a retinal camera unit 1A, an OCT unit 150, and an arithmetic control unit 200 as shown in FIG. 1. The retinal camera unit 1A has almost the same optical system as the conventional retinal cameras for obtaining 2-dimensional images of the fundus oculi surface. The OCT unit 150 houses an optical system that functions as an optical image measurement device. The arithmetic control unit 200 is equipped with a computer for executing various types of arithmetic processes, control processes, or the like.

To the OCT unit 150, one end of a connection line 152 is attached. A connector part 151 for connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

[Configuration of Retinal Camera Unit]

The retinal camera unit 1A is used for forming a 2-dimensional image of the surface of a fundus oculi of an eye, based on optically obtained data (data detected by the imaging devices 10 and 12). Herein, the "2-dimensional image of the surface of the fundus oculi" refers to a color or monochrome image of the surface of the fundus oculi having been obtained, a fluorescent image (a fluorescein angiography image, an indocyanine green fluorescent image, etc.), and the like. As well as the conventional retinal camera, the retinal camera unit 1A is provided with an illumination optical system 100 that illuminates a fundus oculi Ef of an eye to be examined E, and an imaging optical system 120 that guides the fundus oculi reflection light of the illumination light to the imaging device 10.

Although the details will be described later, the imaging device 10 in the imaging optical system 120 of this embodiment detects the illumination light having a wavelength in the near-infrared region. Moreover, this imaging optical system 120 is further provided with the imaging device 12 for detecting the illumination light having a wavelength in the visible region. Moreover, this imaging optical system 120 guides a signal light coming from the OCT unit 150 to the fundus oculi Ef, and guides the signal light passed through the fundus oculi Ef to the OCT unit 150.

The illumination optical system 100 comprises: an observation light source 101; a condenser lens 102; an imaging light source 103; a condenser lens 104; exciter filters 105 and 106; a ring transparent plate 107; a mirror 108; an LCD (Liquid Crystal Display) 109; an illumination diaphragm 110; a relay lens 111; an aperture mirror 112; and an objective lens 113.

The observation light source 101 emits an illumination light having a wavelength of the visible region included in a range of, for example, about 400 nm thorough 700 nm. Moreover, the imaging light source 103 emits an illumination light having a wavelength of the near-infrared region included in a range of, for example, about 700 nm through 800 nm. The near-infrared light emitted from this imaging light source 103 is set so as to have a shorter wavelength than the light used by the OCT unit 150 (described later).

Further, the imaging optical system 120 comprises: an objective lens 113; an aperture mirror 112 (an aperture 112a thereof); an imaging diaphragm 121; barrier filters 122 and 123; a variable magnifying lens 124; a relay lens 125; an imaging lens 126; a dichroic mirror 134; a field lens 128; a half mirror 135; a relay lens 131; a dichroic mirror 136; an imaging lens 133; the imaging device 10 (image pick-up element 10a); a reflection mirror 137; an imaging lens 138; the imaging device 12 (image pick-up element 12a); a lens 139; and an LCD 140.

The dichroic mirror 134 is configured to reflect the fundus oculi reflection light (having a wavelength included in a range of about 400 nm through 800 nm) of the illumination light from the illumination optical system 100, and transmit a signal light LS (having a wavelength included in a range of, for example, about 800 nm through 900 nm; described later) from the OCT unit 150.

Further, the dichroic mirror 136 is configured to transmit the illumination light having a wavelength of the visible region from the illumination optical system 100 (a visible light having a wavelength of about 400 nm through 700 nm emitted from the observation light source 101), and reflect the illumination light having a wavelength of the near-infrared region (a near-infrared light having a wavelength of about 700 nm through 800 nm emitted from the imaging light source 103).

On the LCD 140, a fixation target (internal fixation target) or the like for fixing the eye to be examined E is displayed. The light from this LCD 140 is reflected by the half mirror 135 after being converged by the lens 139, and is reflected by the dichroic mirror 136 through the field lens 128. Then, the light passes through the imaging lens 126, the relay lens 125, the variable magnifying lens 124, the aperture mirror 112 (aperture 112a thereof), the objective lens 113 and the like, and enters the eye to be examined E. Consequently, an internal fixation target or the like is projected in the fundus oculi Ef of the eye to be examined E.

The image pick-up element 10a is an image pick-up element such as a CCD (Charge Coupled Device) and a CMOS (Complementary metal Oxide Semiconductor) installed in the imaging device 10 such as a TV camera, and is particularly used for detecting light having a wavelength of the near-infrared region. In other words, the imaging device 10 is an infrared TV camera for detecting near-infrared light. The imaging device 10 outputs video signals as a result of detection of the near-infrared light.

A touch panel monitor 11 displays a 2-dimensional image (a fundus oculi image Ef') of the surface of the fundus oculi Ef, based on the video signals. The video signals are sent to the arithmetic control unit 200, and the fundus oculi image is displayed on the display (described later).

At the time of imaging of the fundus oculi by the imaging device 10, for example, the illumination light emitted from the imaging light source 103 of the illumination optical system 100 and having a wavelength of the near-infrared region is used.

On the other hand, the image pick-up element 12a is an image pick-up element such as a CCD and a CMOS installed in the imaging device 12 such as a TV camera, and is particularly used for detecting light having a wavelength of the visible region (that is, the imaging device 12 is a TV camera for detecting visible light). The imaging device 12 outputs video signals as a result of detection of the visible light.

The touch panel monitor 11 displays a 2-dimensional image (fundus oculi image Ef') of the surface of the fundus oculi Ef, based on the video signals. The video signals are sent to the arithmetic control unit 200, and the fundus oculi image Ef' is displayed on the display (described later).

At the time of imaging of the fundus oculi by the imaging device 12, for example, the illumination light emitted from the observation light source 101 of the illumination optical system 100 and having a wavelength of the visible region is used.

The retinal camera unit 1A is provided with a scan unit 141 and a lens 142. The scan unit 141 includes a component for scanning at an application position of the fundus oculi Ef with light emitted from the OCT unit (signal light LS; described later).

The lens 142 makes the signal light LS guided from the OCT unit 150 through the connection line 152 enter the scan unit 141 in the form of a parallel light flux. Moreover, the lens 142 acts so as to converge the fundus oculi reflection light of the signal light LS passed through the scan unit 141.

FIG. 2 shows one example of a specific configuration of the scan unit 141. The scan unit 141 comprises Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 6), whereby the orientations of reflection surfaces thereof (faces reflecting the signal light LS), namely, the positions of the Galvano mirrors 141A and 141B are changed, respectively.

The rotary shafts 141a and 141b are arranged so as to be orthogonal to each other. In FIG. 2, the rotary shaft 141a of the Galvano mirror 141A is arranged in parallel to the paper face of FIG. 2, whereas the rotary shaft 141b of the Galvano mirror 141B is arranged so as to be orthogonal to the paper face of FIG. 2.

That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the pair of Galvano mirrors 141A and 141B act so as to change the reflecting directions of the signal light LS to directions orthogonal to each other. As seen from FIGS. 1 and 2, scan with the signal light LS is performed in the x direction when the Galvano mirror 141A is rotated, and scan with the signal light LS is performed in the y direction when the Galvano mirror 141B is rotated.

The signal lights LS reflected by the Galvano mirrors 141A and 141B are reflected by reflection mirrors 141C and 141D, thereby traveling in the same directions as having entered into the Galvano mirror 141A.

As described before, the conductive optical fiber 152a runs through the inside of the connection line 152, and an end face 152b of the optical fiber 152a is arranged facing the lens 142.

The signal light LS emitted from this end face 152b travels while expanding its beam diameter toward the lens 142. The light is converged into a parallel light flux by this lens 142. On the contrary, the signal light LS passed through the fundus oculi Ef is converged toward the end face 152b by the lens 142, and guided to the optical fiber 152a.

[Configuration of OCT Unit]

Next, the configuration of the OCT unit 150 will be described referring to FIG. 3. The OCT unit 150 is a device configured to form a tomographic image of the fundus oculi based on optically obtained data (data detected by a CCD 184 described later).

The OCT unit 150 has almost the same optical system as the conventional optical image measurement device. That is, the OCT unit 150 has: an interferometer that splits the light emitted from the light source into a reference light and a signal light and generates interference-light by superposing the reference light passed through a reference object and the signal light passed through a measurement object (fundus oculi Ef); and a part configured to detect this interference-light and output signals as the result of the detection (detection signals) toward the arithmetic control unit 200. The arithmetic control unit 200 forms a tomographic image of the measurement object (fundus oculi Ef), by analyzing the detection signals.

A low-coherence light source 160 is composed of a broad-band light source, such as a super luminescent diode (SLD) and a light emitting diode (LED), configured to emit a low-coherence light L0. This low-coherence light L0 is, for example, a light that has a wavelength of the near-infrared region and has a time-wise coherence length of approximately several tens of micrometers. The low-coherence light source 160 corresponds to one example of the "light source" of the present invention.

The low-coherence light L0 has a longer wavelength than the illumination light (wavelength: about 400 nm through 800 nm) of the retinal camera unit 1A, for example, a wavelength included in a range of about 800 mm through 900 nm.

The low-coherence light L0 emitted from the low-coherence light source 160 is guided to an optical coupler 162 through an optical fiber 161. The optical fiber 161 is composed of, for example, a single mode fiber or a PM (Polarization maintaining) fiber. The optical coupler 162 splits this low-coherence light L0 into a reference light LR and the signal light LS.

Although the optical coupler 162 acts as both a part (splitter) for splitting light and a part (coupler) for superposing lights, it will be herein referred to as an "optical coupler" idiomatically.

The reference light LR generated by the optical coupler 162 is guided by an optical fiber 163 composed of a single mode fiber or the like, and emitted from the end face of the fiber. The emitted reference light LR is converged into a parallel light flux by a collimator lens 171, passed through a glass block 172 and a density filter 173, and then reflected by a reference mirror 174 (reference object).

The reference light LR reflected by the reference mirror 174 is converged to the fiber end face of the optical fiber 163 by the collimator lens 171 again through the density filter 173 and the glass block 172. The converged reference light LR is guided to the optical coupler 162 through the optical fiber 163.

The glass block 172 and the density filter 173 act as a delaying part for making the optical path lengths (optical distances) of the reference light LR and the signal light LS coincide, and also as a dispersion correction part for making the dispersion characteristics of the reference light LR and the signal light LS coincide.

Further, the density filter 173 also acts as a dark filter for reducing the amount of the reference light, and is composed of a rotating ND (neutral density) filter, for example. This density filter 173 acts so as to change the reduction amount of the reference light LR by being rotary driven by a drive mechanism including a drive unit such as a motor. Consequently, it is possible to change the amount of the reference light LR contributing to generation of the interference-light LC.

Further, the reference mirror 174 is configured so as to move in the traveling direction (the direction of the arrow pointing both sides shown in FIG. 3) of the reference light LR. With this configuration, it is possible to ensure the optical path length of the reference light LR according to the axial length of the eye to be examined E, etc. Moreover, it is possible to capture an image of any depth position of the fundus oculi Ef, by moving the reference mirror 174. The reference mirror 174 is moved by a drive mechanism (a reference mirror driving mechanism 243 described later; referring to FIG. 6) including a driver such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. Herein, the optical fiber 164 and the optical fiber 152a may be composed of a single optical fiber, or may be jointly formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Then, the signal light LS enters into the eye to be examined E through the lens 142, the scan unit 141, the dichroic mirror 134, the imaging lens 126, the relay lens 125, the variable magnifying lens 124, the imaging diaphragm 121, the aperture 112a of the aperture mirror 112, and the objective lens 113. The barrier filter 122 and 123 are retracted from the optical path in advance, respectively, when the signal light LS is made to enter the eye to be examined E.

The signal light LS having entered the eye to be examined E forms an image on the fundus oculi (retina) Ef and is then reflected. At this moment, the signal light LS is not only reflected on the surface of the fundus oculi Ef, but also scattered at the refractive index boundary after reaching the deep area of the fundus oculi Ef. As a result, the signal light LS passed through the fundus oculi Ef is a light containing information reflecting the state of the surface of the fundus oculi Ef and information reflecting the state of backscatter at the refractive index boundary of the deep area tissue of the fundus oculi Ef. This light may be simply referred to as "fundus oculi reflection light of the signal light LS."

The fundus oculi reflection light of the signal light LS travels reversely on the above path within the retinal camera unit 1A, and is converged at the end face 152b of the optical fiber 152a. Then, the signal light LS enters into the OCT unit 150 through the optical fiber 152a, and returns to the optical coupler 162 through the optical fiber 164.

The optical coupler 162 superimposes the signal light LS returning through the fundus oculi Ef and the reference light LR reflected by the reference mirror 174, thereby generating the interference-light LC. The interference light LC is guided to an optical fiber 165 composed of a single mode fiber or the like. Then, the interference light LC exits from the fiber end 165a of the optical fiber 165 and enters the spectrometer 180.

Herein, although a Michelson-type interferometer is adopted in this embodiment, for instance, a Mach Zender type, etc. and any type of interferometer may be adopted appropriately. The "interference-light generator" related to the present invention comprises, for example, an optical coupler 162, an optical member on the optical path of the signal light LS (i.e., an optical member placed between the optical coupler 162 and the fundus oculi Ef), and an optical member on the optical path of the reference light LR (i.e., an optical member placed between the optical coupler 162 and the reference mirror 174), and specifically, comprises an interferometer equipped with the optical coupler 162, the optical fibers 163, 164, and the reference mirror 174.

In addition, the optical fiber 165 functions as an example of the "light guiding part" of the present invention, and the fiber end 165a is equivalent to an example of the "exit end" of the present invention.

The spectrometer 180 comprises a collimator lens 181, a diffraction grating 182, an image-forming lens 183, and a CCD 184. The diffraction grating 182 in this embodiment is a transmission-type diffraction grating that transmits light; however, needless to say, a reflection-type diffraction grating that reflects light may also be used. Moreover, needless to say, it is also possible to adopt, in place of the CCD 184, other photo-detecting elements.

The interference light LC having entered the spectrometer 180 is split (resolved into spectra) by the diffraction grating 182 after converged into a parallel light flux by the collimator lens 181. The split interference light LC forms an image on the image pick-up surface of the CCD 184 by the image-forming lens 183. The CCD 184 receives each spectrum component of dispersed interference light, transforms it into electric signal, and output the transformed signal. The CCD 184 consists of, for example, a CCD line sensor on which a plurality of CCD elements are linearly arranged.

Herein, the diffraction grating 182 functions as an example of the "dispersion part" of the present invention. In addition, the CCD 184 functions as an example of the "light-receiving part" of the present invention.

When measuring, it is required to harmonize the array direction of the CCD elements composing the CCD 184 and the spread direction of spectral components of the interference light LC. In other words, the relative positional relationship between the fiber end 165a and the light-receiving surface of the CCD 184 needs to be adjusted so that each CCD element receives the corresponding spectral component.

A fiber end driving mechanism 244 to be described below alters the position of the fiber end 165a in order to carry out this alignment.

The fiber end driving mechanism 244 is configured to include, for example, an actuator such as a stepping motor and a transmission mechanism that transmits driving force output from this actuator. This transmission mechanism is connected to a site other than the end surface of the optical fiber 165 (i.e., the exit end of the interference light LC) for example, and is adapted to transmit driving force, which the actuator has generated, to the fiber end 165a.

The fiber end driving mechanism 244 moves the fiber end 165a in a direction parallel to the end surface of the optical fiber 165 and in a direction perpendicular to the end surface. As a result, the fiber end 165a is three-dimensionally moved while the orientation of the end surface is fixed. Moreover, the fiber end driving mechanism 244 moves the position of the fiber end 165a so as to alter the orientation of the end surface.

Herein, it is also possible to separately provide an actuator that generates driving force for three-dimensionally moving the end surface and an actuator that generates the driving force for altering the orientation of the end surface. Alternatively, the three-dimensional movement and the altering of the orientation of the end surface may be realized by transmitting driving force generated by a single actuator with separate transmission mechanisms. Alternatively, for the three-dimensional movement, each actuator for moving in each direction may be provided, or the movement in each direction may be realized by transmitting driving force from a single actuator with separate transmission mechanisms. Similarly, also for the altering of the orientation of the end surface, individual actuator may be provided for each direction, or the orientation of the end surface may be altered in each direction by transmitting driving force from a single actuator by separate transmission mechanisms.

An example of a configuration of the fiber end driving mechanism 244 is shown in FIG. 4. The fiber end driving mechanism 244 shown in FIG. 4 moves the fiber end 165a in a direction perpendicular to the longitudinal direction of the optical fiber 165a (the exit direction of the interference light LC).

The fiber end driving mechanism 244 shown in FIG. 4 generates driving force by using the actuator 244a. The actuator 244a functions as an example of the "driving part" of the present invention.

The driving force generated by the actuator 244a is transmitted to a driving force applying member 244b by a transmission mechanism (not shown) and moves the driving force applying member 244b in the direction of the arrows in FIG. 4 (vertically in the page space of FIG. 4). The driving force applying member 244b is connected to an optical fiber holding member 244c. The optical fiber holding member 244c holds the optical fiber 165 at a site in the proximity of the fiber end 165a.

The optical fiber holding member 244c is connected to an end of a piston member 244e at a site opposite the connecting site with the driving force applying member 244b. The piston member 244e is inserted into an opening of a cylinder member 244d, and is configured so as to be movable inside the cylinder member 244d in the direction of the arrows in FIG. 4. Herein, the moving direction of the piston member 244e is the same as the moving direction of the driving force applying member 244b described above. The other end side of the cylinder member 244d, that is the opposite side of the opening, is fixed to an inner wall or the like of the housing of the OCT unit 150.

The site of the piston member 244e that is opposite the connecting site with the optical fiber holding member 244c forms an opening. In other words, the piston member 244e is inserted inside the cylinder member 244d so that the opening is placed in the opening of the cylinder member 244d.

In internal areas of the cylinder member 244d and the piston member 244e, a spring member 244f, which adds elastic force in a direction for putting distance between them, is provided. This added direction of the elastic force is downward in the page space of FIG. 4.

The fiber end driving mechanism 244 configured in this way acts as follows. First, the elastic force due to the spring member 244f is consistently added to the optical fiber holding member 244c downward in the page space of FIG. 4. The driving force generated by the actuator 244a moves the driving force applying member 244b vertically in the page space of the FIG. 4. The optical fiber holding member 244c moves integrally with the driving force applying member 244b. The elastic force due to the spring member 244f acts as a force for sandwiching the optical fiber holding member 244c between the driving force applying member 244b and the piston member 244e. As a result, the optical fiber holding member 244c maintains a static state when not being moved by the driving force from the actuator 244a.

The fiber end 165a of the optical fiber 165 is moved vertically in the page space of FIG. 4 by the fiber end driving mechanism 244 as described above.

Moreover, it is possible to move the fiber end 165a in a direction perpendicular to the page space of FIG. 4 by providing a mechanism that is similar to the fiber end driving mechanism 244 in FIG. 4. As a result, it is possible to two-dimensionally move the fiber end 165a in a direction perpendicular to the longitudinal direction of the optical fiber 165 (the exit direction of the interference light LC).

In addition, the fiber end driving mechanism 244 according to this embodiment may comprise a mechanism for moving, in the longitudinal direction of the optical fiber 165 (the exit direction of the interference light LC), the entire fiber driving mechanism that enables such two-dimensional movement. This makes it possible, when the optical distance between the fiber end 165a and the CCD 184 is out of alignment, or the like, to correct the distance between them.

Moreover, the fiber end driving mechanism 244 according to this embodiment may also comprise a mechanism (inclining mechanism) for inclining the entire fiber driving mechanism that enables three-dimensional movement as above (three-dimensional moving mechanism). This makes it possible to alter the orientation of the end surface of the fiber end 165a and alter the exit direction of the interference light LC.

Moreover, a three-dimensional moving mechanism that three-dimensionally moves the entire inclining mechanism for altering the orientation of the end surface of the fiber end 165a may be provided. At any rate, the fiber end driving mechanism 244 according to this embodiment is configured so as to three-dimensionally move the fiber end 165a, and act to alter the orientation of the end surface of the optical fiber 165a.

The fiber end driving mechanism 244 (and a controller 210 that controls the same) is equivalent to an example of the "altering part" of the present invention. Moreover, this altering part only has to be capable of performing at least one operation of: three one-dimensional movements for the abovementioned three-dimensional movement and the abovementioned altering of the orientation of the end surface. In this regard, however, the positional misalignment between the fiber end 165a and the light-receiving surface of the CCD 184 occurs in practically any direction, so the degree of freedom of the moving direction of the fiber end 165a by the fiber end driving mechanism 244 is preferably larger.

[Configuration of Arithmetic Control Unit]

Next, the configuration of the arithmetic control unit 200 will be described. The arithmetic control unit 200 performs a process of analyzing detection signals entered from the CCD 184 of the spectrometer 180 of the OCT unit 150 and forming a tomographic image of the fundus oculi Ef of the eye to be examined E. The analysis method is the same as the conventional technique of Fourier Domain OCT.

Further, the arithmetic control unit 200 performs a process of forming (image data of) a 2-dimensional image showing the state of the surface (retina) of the fundus oculi Ef, based on the video signals outputted from the imaging devices 10 and 12 of the retinal camera unit 1A.

Furthermore, the arithmetic control unit 200 executes control of each part of the retinal camera unit 1A and the OCT unit 150.

The arithmetic control unit 200 executes as control of the retinal camera unit 1A, for example: control of emission of illumination light by the observation light source 101 or the imaging light source 103; control of insertion/retraction operations of the exciter filters 105 and 106 or the barrier filters 122 and 123 to/from the optical path; control of the operation of a display device such as the LCD 140; control of shift of the illumination diaphragm 110 (control of the diaphragm value); control of the diaphragm value of the imaging diaphragm 121; and control of shift of the variable magnifying lens 124 (control of the magnification). Moreover, the arithmetic control unit 200 executes control of the operation of the Galvano mirrors 141A and 141B inside the scan unit 141 (operation of changing the directions of the reflection faces).

Further, the arithmetic control unit 200 executes as control of the OCT unit 150, for example: output control of the low coherent light L0 via the low coherent light source; moving control of the reference mirror 174; control of rotational action (an action to change reduced amount of the reference light LR); control of accumulation time of CD 184; control of the positional relationship between the fiber end 165a of the optical fiber 165 and the CCD 184, or the like.

Moreover, in this embodiment, it is adapted to alter the positional relationship between the fiber end 165a and the CCD 184 by controlling the fiber end driving mechanism 244 to alter the position (including the orientation) of the fiber end 165a of the optical fiber 165.

When the actuator of the fiber end driving mechanism 244 is a stepping motor, the arithmetic and control device 200 (controller 210) sends a pulse signal to this stepping motor. The stepping motor operates to move the fiber end 165a in the intended direction by a distance depending on the pulse number of this pulse signal, and operates to alter the orientation of the fiber end 165a (end surface) by an angle depending on the pulse number.

Moreover, the moving distance (unit moving distance) and inclined angle (unit inclined angle) corresponding to one pulse are set in advance. The arithmetic and control device 200 (controller 210) controls the position of the fiber end 165a by sending a pulse signal including the pulse number depending on the intended moving distance or inclined angle to the fiber end driving mechanism 244.

One example of the hardware configuration of the arithmetic and control unit 200 that acts as described above will be described referring to FIG. 5.

The arithmetic and control unit 200 is provided with the same hardware configuration as that of a conventional computer. To be specific, the arithmetic and control unit 200 comprises: a microprocessor 201 (CPU, MPU, etc.), a RAM 202, a ROM 203, a hard disk drive (HDD) 204, a keyboard 205, a mouse 206, a display 207, an image forming board 208, and a communication interface (I/F) 209. These parts are connected via a bus 200a.

The microprocessor 201 comprises a CPU (Central Processing Unit), an MPU (Micro Processing Unit) or the like, and executes operations characteristic to this embodiment, by loading a control program 204a stored in the hard disk drive 204, onto the RAM 202. Further, the microprocessor 201 executes control of each part of the device described above, various arithmetic processes, etc. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206 and the display 207 are used as user interfaces in the fundus oculi observation device 1. The keyboard 205 is used as, for example, a device for typing letters, figures, etc. The mouse 206 is used as a device for performing various input operations to the display screen of the display 207.

Further, the display 207 is any display device composed of an LCD, a CRT (Cathode Ray Tube) display or the like. The display 207 displays various images of the fundus oculi Ef formed by the fundus oculi observation device 1, and displays various screens such as an operation screen and a set-up screen.

The user interface of the fundus oculi observation device 1 is not limited to the above configuration, and may be configured by using any user interface having a function of displaying and outputting various information, and a function of entering various information and operating the device, such as a track ball, a control lever, a touch panel type of LCD, and a control panel for opthalmology examinations.

The image forming board 208 is a dedicated electronic circuit for a process of forming (image data of) images of the fundus oculi Ef of the eye to be examined. This image forming board 208 is provided with a fundus oculi image forming board 208a and an OCT-image forming board 208b.

The fundus oculi image forming board 208a is a dedicated electronic circuit that operates to form image data of fundus oculi images based on the video signals from the imaging device 10 and the imaging device 12 of the retinal camera unit 1A.

Further, the OCT-image forming board 208b is a dedicated electronic circuit that operates to form image data of tomographic images of the fundus oculi Ef, based on the detection signals from the CCD 184 of the spectrometer 180 in the OCT unit 150.

By providing the image forming board 208, it is possible to increase the processing speed for forming image data of fundus oculi images and tomographic images.

The communication interface 209 performs a process of sending control signals from the microprocessor 201, to the retinal camera unit 1A or the OCT unit 150. Moreover, the communication interface 209 performs a process of receiving video signals from the imaging devices 10 and 12 of the retinal camera unit 1A and detection signals from the CCD 184 of the OCT unit 150, and entering the signals to the image forming board 208. At this time, the communication interface 209 operates to enter the video signals from the imaging devices 10 and 12, to the fundus oculi image forming board 208a, and enter the detection signal from the CCD 184, to the OCT-image forming board 208b.

Further, in a case where the arithmetic and control unit 200 is connected to a network such as a LAN (Local Area Network) and the Internet, it is possible to configure so as to be capable of data communication via the network, by providing the communication interface 209 with a network adapter like a LAN card or communication equipment like a modem. In this case, by mounting a server accommodating the control program 204a on the network, and at the same time, configuring the arithmetic and control unit 200 as a client terminal of the server, it is possible to cause the fundus oculi observation device 1 to execute the operation according to the present invention.

[Configuration of Control System]

Next, the configuration of the control system of the fundus oculi observation device I will be described referring to FIG. 6 and FIG. 7. FIG. 6 is a block diagram showing a part related to the operations and processes according to the present invention particularly selected from among constituents composing the fundus oculi observation device 1. FIG. 7 shows one example of the configuration of the operation panel 3a disposed to the retinal camera unit 1A.

(Controller)

The control system of the fundus oculi observation device 1 is configured mainly having a controller 210 of the arithmetic and control unit 200 shown in FIG. 6. The controller 210 comprises the microprocessor 201, the RAM 202, the ROM 203, the hard disk drive 204 (control program 204a), and the communication interface 209.

The controller 210 executes the aforementioned controlling processes through the microprocessor 201 operating based on the control program 204a. In specific, for the retinal camera unit 1A, the controller 210 performs control of the mirror drive mechanisms 241 and 242 for changing the positions of the Galvano mirrors 141A and 141B.

Further, for the OCT unit 150, the controller 210 performs control of the low-coherence light source 160 and the CCD 184, the control of the fiber end driving mechanism 244 that alters the position of the fiber end 165a of the optical fiber 165, control of the reference-mirror driving mechanism 243 for moving the reference mirror 174 in the traveling direction of the reference light LR, etc. The controller 210 is configured to adjust the positional relationship between the fiber end 165a and the CCD 184 by altering the position of the fiber end 165a as described above, and is equivalent to an example of the "control part" of the present invention.

Moreover, in this embodiment, it is configured to adjust the positional relationship between the fiber end 165a and the CCD 184 by moving the position of the fiber end 165a. On the other hand, it is also possible to apply a configuration for moving the position of the CCD 184 (light-receiving surface) or a configuration for moving both the fiber end 165a and the CCD 184. At any rate, it only has to be configured so as to be capable of altering the relative position of the fiber end 165a of the optical fiber 165 that guides the interference light LC and the CCD 184 or the spectrometer 180.

Furthermore, the controller 210 performs control for causing the display 240A of the user interface (UI) 240 to display two kinds of images obtained by the fundus oculi observation device 1: that is, a 2-dimensional image of the surface of the fundus oculi Ef obtained by the retinal camera unit 1A, and a tomographic image of the fundus oculi Ef formed based on the detection signals obtained by the OCT unit 150. These images may be displayed on the display 240A separately, or may be displayed side by side simultaneously.

(Irradiation State Specifying Part)

The controller 210 is provided with an irradiation state specifying part 211. The irradiation state specifying part 211 is configured to specify the irradiation state of the interference light LC onto the light-receiving surface of the CCD 184, and functions as an example of the "specifying part" of the present invention. Herein, the "irradiation state" may include an irradiating position of the interference light LC onto the light-receiving surface of the CCD 184 and an irradiating direction of the interference light LC onto the light-receiving surface.

When the irradiating position of the interference light LC onto the light-receiving surface is out of alignment, some or all of the CCD elements that are arrayed on the light-receiving surface cannot receive the interference light LC. Therefore, it is impossible to detect some or all of spectral components of the interference light LC and form an OCT image. In addition, when the irradiating direction of the interference light LC onto the light-receiving surface is out of alignment, each spectral component of the interference light LC enters the CCD elements that are arrayed on the light-receiving surface from an improper direction. Therefore, the amount of light received of the spectral components detected by each CCD element does not reflect the actual light amount (intensity), thereby making it impossible to form a proper OCT image.

The irradiation state specifying part 211 has a function for determining whether the problem as above occurs or not, by specifying the irradiation state of the interference light LC onto the light-receiving surface. Hereinafter, an example of the operations of the irradiation state specifying part 211 will be explained.

The specifying process of the irradiation state of the interference light LC is carried out by using the results of the measurement as follows. The CCD 184 receives light that has exited the fiber end 165a and has been dispersed by the diffraction grating 182, and sends the light-receiving result to the arithmetic and control device 200. The light to be employed in this measurement (to be referred to as measurement light) may be the interference light LC or other light. As other light, for example, the reference light LR that is based on the low-coherence light L0 may be employed. This reference light LR as measurement light can be obtained by outputting the low-coherence light L0 without disposing the object to be measured on the measurement position. In addition, a dedicated light source that outputs measurement light may also be provided.

The irradiation state specifying part 211 specifies the light-receiving amount of measurement light by analyzing the light-receiving result of measurement light by the CCD 184. For this purpose, for example, the irradiation state specifying part 211 stores a appropriate value of the light-receiving amount of detected light in advance.

Herein, "proper" implies a state in which measurement light is properly irradiated onto the light-receiving surface of the CCD 184, that is, a state in which each spectral component of measurement light is irradiated onto a predetermined position on the light-receiving surface. In such a proper irradiation state, it is possible to preferably form an OCT image. Moreover, it is assumed that any misalignment of measurement light within a range in which an OCT image can be preferably obtained is allowed.

This proper value is information that represents, for example, the spectral distribution of measurement light, that is, the proper light-receiving amount for each spectrum. In other words, this proper value is information that represents the distribution of the light-receiving amount by a plurality of CCD elements of the CCD 184 while measurement light is properly irradiated. This proper value can be obtained by actually aligning the light-receiving surface of the CCD 184 and the fiber end 165a of the optical fiber 165, and, in this state, actually measuring the light-receiving amount of measurement light. Moreover, it is also possible to theoretically find the proper value based on the emitted light amount of measurement light, the configuration of the optical system of the OCT unit 150, or the like.

The irradiation state specifying part 211 specifies an irradiating position of measurement light onto the light-receiving surface of the CCD 184, that is, an irradiating position of the interference light LC by comparing the light-receiving amount of measurement light by the CCD 184 with the proper value. The irradiation state specifying part 211 can determine misalignment of the irradiating position of measurement light as follows by comparing the distribution of the light-receiving amount of measurement light due to the plurality of CCD elements of the CCD 184 with the distribution of the light-receiving amount indicated by the proper value. Herein, the CCD 184 is assumed to be a CCD line sensor.

First, when both light-receiving amounts are distributed at almost the same position in the array direction of the CCD elements, and the light-receiving amounts due to a plurality of CCD elements are almost uniformly smaller than the proper value, the irradiating position of measurement light can be determined to be out of alignment in a direction perpendicular to the array direction (widthwise), although misalignments in the array direction of the CCD elements can be allowed.

Moreover, it is possible to specify the direction or size of misalignments widthwise based on the value of the light-receiving amount of measurement light compared to the proper value. For example, when the light-receiving amount is half the proper value, it can be determined that the irradiating position is out of alignment by a distance of half the length widthwise of the CCD element. Moreover, when the CCD 184 cannot receive measurement light at all, it is desirable to control the movement of the fiber end 165a until measurement light comes to be received even if only a little.

In addition, when the distribution of the light-receiving amount of measurement light is out of alignment in the array direction of the CCD elements compared to the distribution indicated by the proper value, it can be determined that the irradiating position of measurement light is out of alignment in the array direction of the CCD elements.

Furthermore, it is possible to specify the direction or size of misalignments in the array direction by finding the displacement of the distribution of both in the array direction, that is, how many CCD elements it is displaced by. For example, when it is displaced by a distance of ten CCD elements, it can be determined that the irradiating position is out of alignment by a distance of ten times the length of the array direction of the CCD element.

Moreover, when the irradiating position of measurement light is out of alignment in the array direction, the CCD 184 may not be capable of receiving all spectral components of measurement light, and in that case, distribution of only a portion can be obtained. Therefore, it is also possible to specify the misalignment in the array direction of the irradiating position of measurement light by figuring out which portion of the entire distribution the obtained distribution is equivalent to.

Next, a process for specifying an irradiating direction of measurement light (interference light LC) onto the light-receiving surface of the CCD 184 will be explained. When the irradiating direction of measurement light is out of alignment from the proper direction, differences arise in the light-receiving amount of the spectral components of measurement light. In other words, compared to the case in which measurement light is irradiated from the proper direction, the distribution of the spectra forms an inclined shape.

The irradiation state specifying part 211 stores in advance information that represents the difference of the light-receiving amount when measurement light is properly irradiated onto the light-receiving surface of the CCD 184 (proper value). Moreover, the irradiation state specifying part 211 determines how much the distribution of the light-receiving amount of spectral components of measurement light inclines compared to the proper value, and specifies an irradiating direction of measurement light based on this inclined angle.

(Image Forming Part)

An image forming part 220 performs a process of forming image data of the fundus oculi image based on the video signals from the imaging devices 10 and 12 of the retinal camera unit 1A, and a process of forming image data of the tomographic images of the fundus oculi Ef based on the detection signals from the CCD 184 of the OCT unit 150.

The imaging forming part 220 comprises the imaging forming board 208 and the communication interface 209. In this specification, "image" may be identified with "image data" corresponding thereto.

(Image Processor)

The image processor 230 applies various image processing and analysis process to image data of images formed by the image forming part 220. For example, the image processor 230 executes various correction processes such as brightness correction and dispersion correction of the images.

In addition, the image processor 230 applies an interpolation process for interpolating pixels between tomographic images to tomographic images that have been formed by the image forming part 220, in order to form image data of a three-dimensional image of the fundus oculi Ef.

Herein, image data of a 3-dimensional image is image data made by assigning pixel values to each of a plurality of voxels arranged 3-dimensionally, and is referred to as volume data, voxel data, and the like. When displaying an image based on volume data, the image processor 230 operates to apply a rendering process (such as volume rendering and MIP (Maximum Intensity Projection)) to this volume data and form image data of a pseudo 3-dimensional image seen from a specified viewing direction. On the display part 240A, the pseudo 3-dimensional image based on the image data is displayed.

Moreover, the image processor 230 is also capable of forming stack data of a plurality of tomographic images. The stack data is image data that is obtained by arraying a plurality of tomographic images that have been obtained along a plurality of scanning lines, based on the positional relationship between the scanning lines.

The image processor 230 that operates as described above comprises the microprocessor 201, the RAM 202, the ROM 203, and the hard disk drive 204 (control program 204a).

(User Interface)

The user interface (UI) 240 comprises the display 240A and an operation part 240B. The display 240A is composed of a display device such as the display 207. Further, the operation part 240B is composed of an input device or an operation device such as the keyboard 205 and the mouse 206.

(Operation Panel)

The operation panel 3a of the retinal camera unit 1A will be described. The operation panel 3a is arranged on the platform (not shown) of the retinal camera unit 1A, for example.

The operation panel 3a is provided with an operating part used to instruct an operation for capturing a 2-dimensional image of the surface of the fundus oculi Ef, and an operating part used to instruct an operation for capturing a tomographic image of the fundus oculi Ef.

Placement of the operation panel 3a makes it possible to execute an operation for capturing a fundus oculi image Ef' and an operation for capturing a tomographic image in the same manner as when operating a conventional retinal camera.

As shown in FIG. 7, the operation panel 3a is provided with, for example, a menu switch 301, a split switch 302, an imaging light amount switch 303, an observation light amount switch 304, a jaw holder switch 305, a imaging switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a certain menu screen for a user to select and designate various menus (such as an imaging menu for imaging a 2-dimensional image of the surface of the fundus oculi Ef, a tomographic image and 3-dimensional image the like, and a setting menu for entering various settings).

When this menu switch 301 is operated, the operation signal is entered to the controller 210. The controller 210 causes the touch panel monitor II or the display 240A to display a menu screen, in response to the input of the operation signal. A controller (not shown) may be provided in the retinal camera unit 1A, whereby the controller causes the touch panel monitor 11 to display the menu screen.

The split switch 302 is a switch operated to switch the light on and off of the split bright line for focusing (e.g., see Japanese Unexamined Patent Application Publication JP-A 9-66031. Also referred to as split target, split mark and so on.). The configuration for projecting this split bright line onto the eye to be examined (split bright line projection part) is housed, for example, in the retinal camera unit 1A (not shown in FIG. 1).

When this split switch 302 is operated, the operation signal is entered to the controller 210 (or the aforementioned controller inside the retinal camera unit 1A; the same hereinafter). The controller 210 projects the split bright line onto the eye to be examined by controlling the split bright line projection part, in response to the input of this operation signal.

The imaging light amount switch 303 is a switch operated to adjust the emitted light amount of the imaging light source 103 (imaging light amount) depending on the state of the eye to be examined (such as the degree of opacity of the lens). This imaging light amount switch 303 is provided with, for example, an imaging light amount increasing switch "+" for increasing the imaging light amount, a imaging light amount decreasing switch "−" for decreasing the imaging light amount, and a reset switch (a button in the middle) for setting the imaging light amount to a predetermined initial value (default value).

When one of the imaging light amount switches 303 is operated, the operation signal is entered to the controller 210. The controller 210 controls the imaging light source 103 in response to the entered operation signal and adjusts the imaging light amount.

The observation light amount switch 304 is a switch operated to adjust the emitted light amount (observation light amount) of the observation light source 101. The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, the operation signal is entered to the controller 210. The controller 210 controls the observation light source 101 in response to the entered operation signal and adjusts the observation light amount.

The jaw holder switch 305 is a switch to move the position of the jaw holder (not shown) of the retinal camera unit 1A. This jaw holder switch 305 is provided with, for example, an upward movement switch (upward triangle) for moving the jaw holder upward, and a downward movement switch (downward triangle) for moving the jaw holder downward.

When one of the jaw holder switches 305 is operated, the operation signal is entered to the controller 210. The controller 210 controls a jaw holder movement mechanism (not shown) in response to the entered operation signal and moves the jaw holder upward or downward.

The imaging switch 306 is a switch used as a trigger switch for capturing a 2-dimensional image of the surface of the fundus oculi Ef or a tomographic image of the fundus oculi Ef.

When the imaging switch 306 is operated in a state where a menu to obtain a 2-dimensional image is selected, the controller 210 that has received the operation signal controls the imaging light source 103 to emit imaging illumination light, and also causes the display 240A or the touch panel monitor 11 to display a 2-dimensional image of the surface of the fundus oculi Ef, based on the video signal outputted from the imaging device 10 having detected the fundus oculi reflection light.

On the other hand, when the imaging switch 306 is operated in a state where a menu to capture a tomographic image is selected, the controller 210 that has received the operation signal controls the low-coherence light source 160 to emit the low-coherence light L0, and also controls the Galvano mirrors 141A and 141B to scan the signal light LS. Moreover, the controller 210 causes the display 240A or the touch panel monitor II to display a tomographic image of the fundus oculi Ef formed by the image forming part 220 (and image processor 230), based on the detection signal outputted from the CCD 184 that has detected the interference light LC. When the menu for obtaining 3-dimensional image is selected, a 3-dimensional image of the fundus oculi Ef based on a plurality of similarly obtained tomographic images is displayed on the display 240A.

The zoom switch 307 is a switch operated to change the angle of view (zoom magnification) at the time of imaging the fundus oculi Ef. Every time this zoom switch 307 is operated, the imaging angle is set alternately to 45 degrees and 22.5 degrees, for example.

When this zoom switch 307 is operated, the controller 210 that has received the operation signal controls a variable magnifying lens driving mechanism (not shown) to move the variable magnifying lens 124 in the optical axis direction of the imaging optical system 120, thereby changing the imaging angle of view.

The image switching switch 308 is a switch operated to switch displayed images. When the image switching switch 308 is operated in a state where a fundus oculi observation image (a 2-dimensional image of the surface of the fundus oculi Ef based on the video signal from the imaging device 12) is displayed on the display 240A or the touch panel monitor 11, the controller 210 having received the operation signal controls the display 240A or touch panel monitor 11 to display the tomographic image of the fundus oculi Ef.

On the other hand, when the image-switching switch 308 is operated in a state where a tomographic image of the fundus oculi is displayed on the display 240A or the touch pane monitor 11, the controller 210 having received the operation signal controls the display 240A or the touch panel monitor 11 to display the fundus oculi observation image.

The fixation target-switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi (fixation position for fundus oculi center imaging)," "fixation position to capture the image of the peripheral region of macula lutea (fixation position for macula lutea imaging)" and "fixation position to capture the image of the peripheral region of papilla (fixation position for papilla imaging)," in a circulative fashion.

In response to the operation signals from the fixation target-switching switch 309, the controller 210 causes the LCD 140 to display the internal fixation target in different positions on the display surface thereof. The display positions of the internal fixation target corresponding to the above three fixation positions, for example, can be preset based on clinical data, or can be set for each eye or for each image imaging in advance.

The fixation target position-adjusting switch 310 is a switch operated to adjust the display position of the internal fixation target. This fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from either of these switches of the fixation target position-adjusting switch 310, the controller 210 controls the LCD 140 to move the display position of the internal fixation target, in response to the operation signal.

The fixation target size switching switch 311 is a switch operated to change the size of the internal fixation target. When this fixation target size switching switch 311 is operated, the controller 210 that has received the operation signal controls the LCD 140 to change the display size of the internal fixation target. The display size of the internal fixation target can be switched, for example, between "normal size" and "enlarged size," alternately. As a result, the size of the projection image of the fixation target projected onto the fundus oculi Ef is changed. Upon reception of the operation signal from the fixation target position adjusting switch 311, the controller 210 controls the LCD 140 to change the display size of the internal fixation target, in response to the operation signal.

The mode-switching knob 312 is a knob rotationally operated to select various imaging modes. The imaging modes are, for example, a fundus oculi imaging mode to obtain a 2-dimensional image of the fundus oculi Ef, a B-scan mode to perform B-scan of the signal light LS, an radial scanning mode for radially scanning the signal light LS, and a 3-dimensional scan mode to scan with the signal light LS 3-dimensionally. In addition, the mode-switching knob 312 may be configured so as to be capable of selecting a replay mode to replay and display a captured 2-dimensional image or tomographic image of the fundus oculi Ef. In addition, it may be configured so as to be capable of selecting a imaging mode to control so that imaging the fundus oculi Ef would be performed immediately after scanning of the signal light LS. Control of each part of the device for causing the fundus oculi observation device 1 to execute the operation corresponding to the each mode is executed by the controller 210.

[Signal Light Scanning]

Scanning of the signal light LS is performed by changing the positions (directions of the reflecting surfaces) of the Galvano mirrors 141A and 141B of the scan unit 141 in the retinal camera unit 1A. By controlling the mirror drive mechanisms 241 and 242 respectively to change the directions of the reflecting surfaces of the Galvano mirrors 141A and 141B respectively, the controller 210 scans the application position of the signal light LS on the fundus oculi Ef.

When the facing direction of the reflecting surface of the Galvano mirror 141A is changed, the signal light LS is scanned in the horizontal direction (x-direction in FIG. 1) on the fundus oculi Ef. Whereas, when the facing direction of the reflecting surface of the Galvano mirror 141B is changed, the signal light LS is scanned in the vertical direction (y-direction in FIG. 1) on the fundus oculi Ef. Further, by changing the facing directions of the reflecting surfaces of both the Galvano mirrors 141A and 141B simultaneously, it is possible to scan the signal light LS in the composed direction of the x-direction and y-direction. That is, by controlling these two Galvano mirrors 141A and 141B, it is possible to scan the signal light LS in any direction on the x-y plane.

Figure 8A:
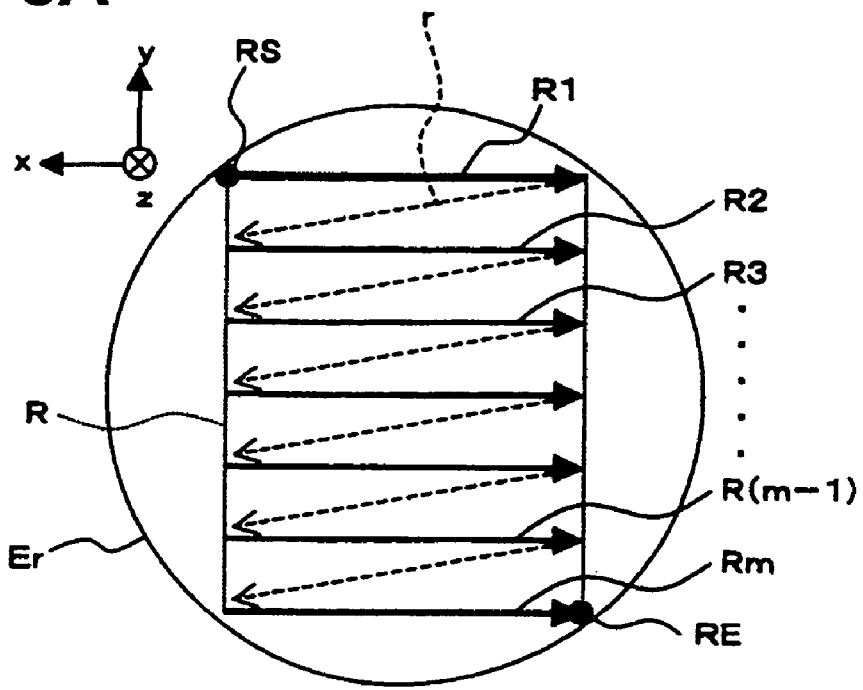
FIG. 8 is a schematic diagram showing one example of the scanning pattern of a signal light in the preferred embodiment of the device related to the present invention.
Figure 8B:
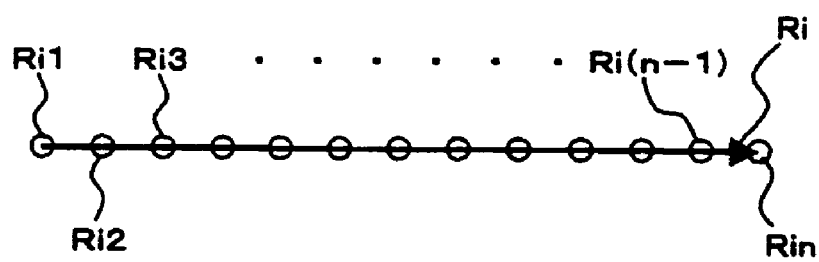

FIGS. 8A and 8B shows one example of the feature of scanning of the signal light LS for forming images of the fundus oculi Ef. FIG. 8A shows one example of the feature of scanning of the signal light LS, when the fundus oculi Ef is seen from a direction that the signal light LS enters the eye to be examined (that is, seen from −z side toward +z side in FIG. 1). Further, FIG. 8B shows one example of the feature of arrangement of scanning points (positions at which image measurement is carried out; target positions of the signal light LS) on each scanning line on the fundus oculi Ef.

The signal light LS, for example, within a rectangular scanning region R as shown in FIG. 8(A), is scanned. Within this scanning region R, a plurality of (m number of) scanning lines R1 through Rm are set in the x-direction. When the signal light LS is scanned along the respective scanning lines Ri (i=1 through m), detection signals of the interference light LC are generated.

Herein, a direction of each scanning line Ri will be referred to as the "main scanning direction" and a direction orthogonal thereto will be referred to as the "sub-scanning direction". Accordingly, scanning of the signal light LS in the main scanning direction is performed by changing the facing direction of the reflecting surface of the Galvano mirror 141A, and scanning in the sub-scanning direction is performed by changing the facing direction of the reflecting surface of the Galvano mirror 141B.

On each scanning line Ri, as shown in FIG. 8B, a plurality of (n number of) scanning points Ri1 through Rin are preset.

In order to execute the scanning shown in FIGS. 8A and 8B, the controller 210 firstly controls the Galvano mirrors 141A and 141B to set the target of the signal light LS entering into the fundus oculi Ef to a scan start position RS (scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of this signal light LS at the scan start position RS, and outputs the detection signal to the arithmetic and control device 200.

Next, the controller 210 controls the Galvano mirror 141A to scan the signal light LS in the main scanning direction and set the incident target of the signal light LS to a scanning point R12, and makes the low-coherence light L0 flushed to make the signal light LS enter into the scanning point R12. The CCD 184 receives the interference light LC based on the fundus oculi reflection light of this signal light LS at the scanning point R12, and then outputs the detection signal to the arithmetic and control device 200.

Likewise, the controller 210 obtains detection signals outputted from the CCD 184 in response to the interference light LC for each scanning point, by flushing the low-coherence light L0 at each scanning point while shifting the incident target of the signal light LS from scanning point R13 to R14, - - -, R1 (n−1), and R1n in order.

Once the measurement at the last scanning point R1n of the first scanning line R1 is finished, the controller 210 controls the Galvano mirrors 141A and 141B simultaneously to shift the incident target of the signal light LS to the first scanning point R21 of the second scanning line R2 following a line switching scan r. Then, by conducting the previously described measurement on each scanning point R2j (j=1 through n) of this second scanning line R2, detection signals corresponding to the respective scanning points R2j are obtained.

Likewise, the measurement is conducted for each of the third scanning line R3, - - -, the m-1th scanning line R(m−1), the mth scanning line Rm to obtain the detection signals corresponding to the respective scanning points. Symbol RE on a scanning line Rm is a scan end position corresponding to a scanning point Rmn.

As a result, the controller 210 obtains m×n number of detection signals corresponding to m×n number of scanning points Rij (i=1 through m, j=1 through n) within the scanning region R. Hereinafter, a detection signal corresponding to the scanning point Rij may be represented by Dij.

Such interlocking control of the shift of scanning points and the emission of the low-coherence light L0 can be realized by synchronizing, for instance, timing for transmission of control signals to the mirror drive mechanisms 241 and 242 and timing for transmission of control signals (output request signals) to the low-coherence light source 160.

As described above, when each of the Galvano mirrors 141A and 141B is operated, the controller 210 stores the position of each scanning line Ri and the position of each scanning point Rij (coordinates on the x-y coordinate system) as information representing the content of the operation. This stored content (scanning point coordinate information) is used in an image forming process as in conventional one.

[Image Processing]

Figure 9:
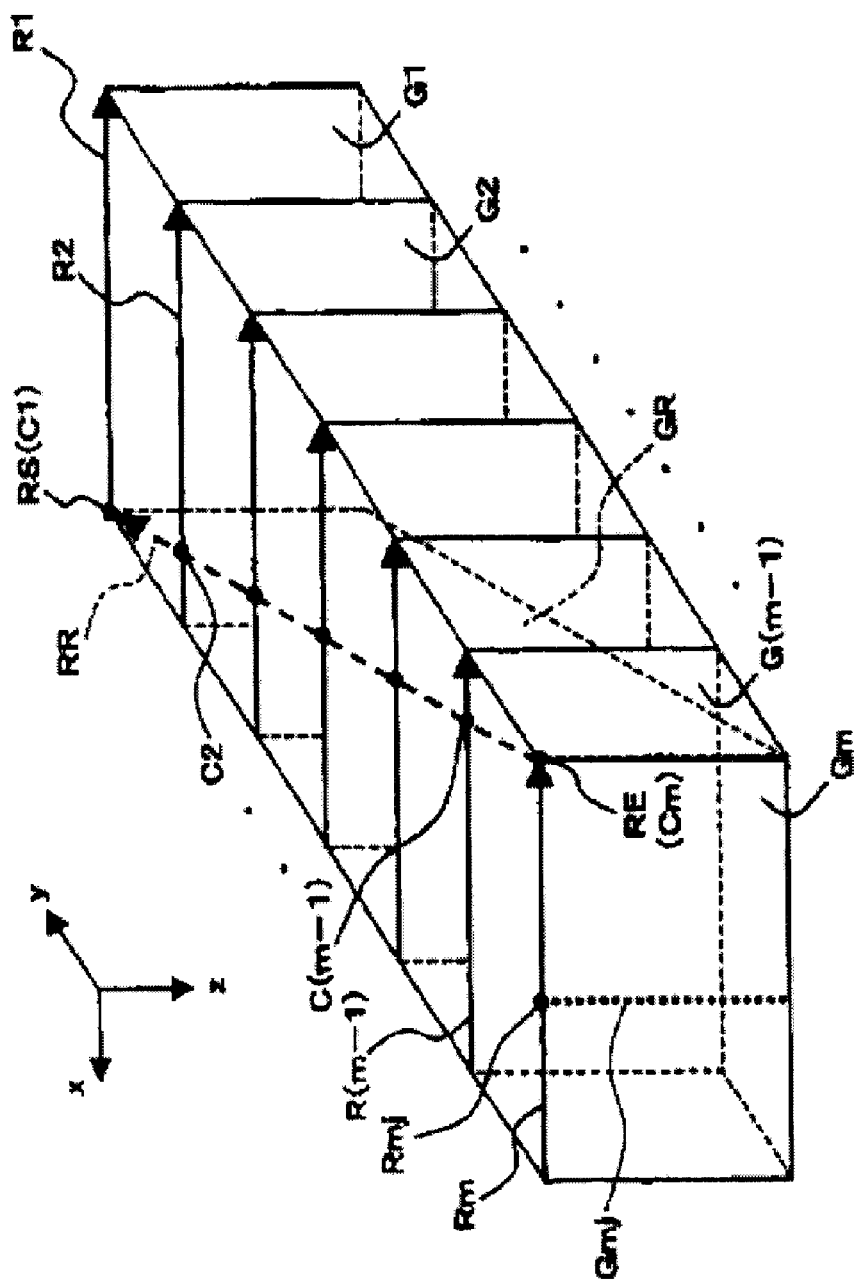
FIG. 9 is a schematic diagram showing one example of the scanning pattern of a signal light in the preferred embodiment of the device related to the present invention.

Next, with reference to FIG. 9, one example of a process on OCT images (tomography images of the fundus oculi Ef) by the image forming part 220 and the image processor 230 will be described.

As described above, the image forming part 220 executes the formation process of tomographic images of the fundus oculi Ef along each scanning line Ri (main scanning direction). Further, the image processor 230 executes the formation process of a 3-dimensional image of the fundus oculi Ef based on these tomographic images formed by the image forming part 220, etc.

The formation process of a tomographic image by the image forming part 220, as in the conventionally one, includes a 2-step arithmetic process. In the first step of the arithmetic process, based on a detection signal Dij corresponding to each scanning point Rij, an image Gij in the depth-wise direction (z-direction in FIG. 1) of the fundus oculi Ef at the scanning point Rij is formed. The image Gij depthwise is a one-dimensional image that passes through the scanning point Rij and extends in the z direction. Moreover, in FIG. 9, only the image Gmj depthwise at the scanning point Rmj is described.

In the second step of the arithmetic process, on each scanning line Ri, by lining up the images in the depth-wise direction at the n number of scanning points Ri1 through Rin, a tomographic image Gi of the fundus oculi Ef along the scanning line Ri is formed. Then, the image forming part 220 determines the arrangement and the distance of the scanning points Ri1 through Rin referring to the positional information (scanning point coordinate information described before) of the scanning points Ri1 through Rin, and forms a tomographic image Gi along this scanning line Ri.

Through the above process, m number of tomographic images G1 through Gm at different positions in the sub-scanning direction (y-direction) are obtained.

Next, the formation process of a 3-dimensional image of the fundus oculi Ef by the image processor 230 will be explained. A 3-dimensional image of the fundus oculi Ef is formed based on the m number of tomographic images obtained through the above arithmetic process. The image processor 230 forms a 3-dimensional image of the fundus oculi Ef by performing a known interpolating process to interpolate an image between the adjacent tomographic images. For this 3-dimensional image, 3-dimensional coordinate is set based on a positional information of each scanning point Rij (the coordinate information of scanning point described above) and z-coordinate depthwise.

Furthermore, based on this 3-dimensional image, the image processor 230 can form a tomographic image of the fundus oculi Ef at a cross-section in any direction other than the main scanning direction (x-direction). Once the cross-section is designated, the image processor 230 determines the position of each scanning point (and/or an interpolated depth-wise image) on this designated cross-section, and extracts a depth-wise image at each determined position (and/or an interpolated depth-wise image), thereby forming a tomographic image of the fundus oculi Ef at the designated cross-section by arranging plural extracted depth-wise images.

Aspect of Usage

Figure 10:
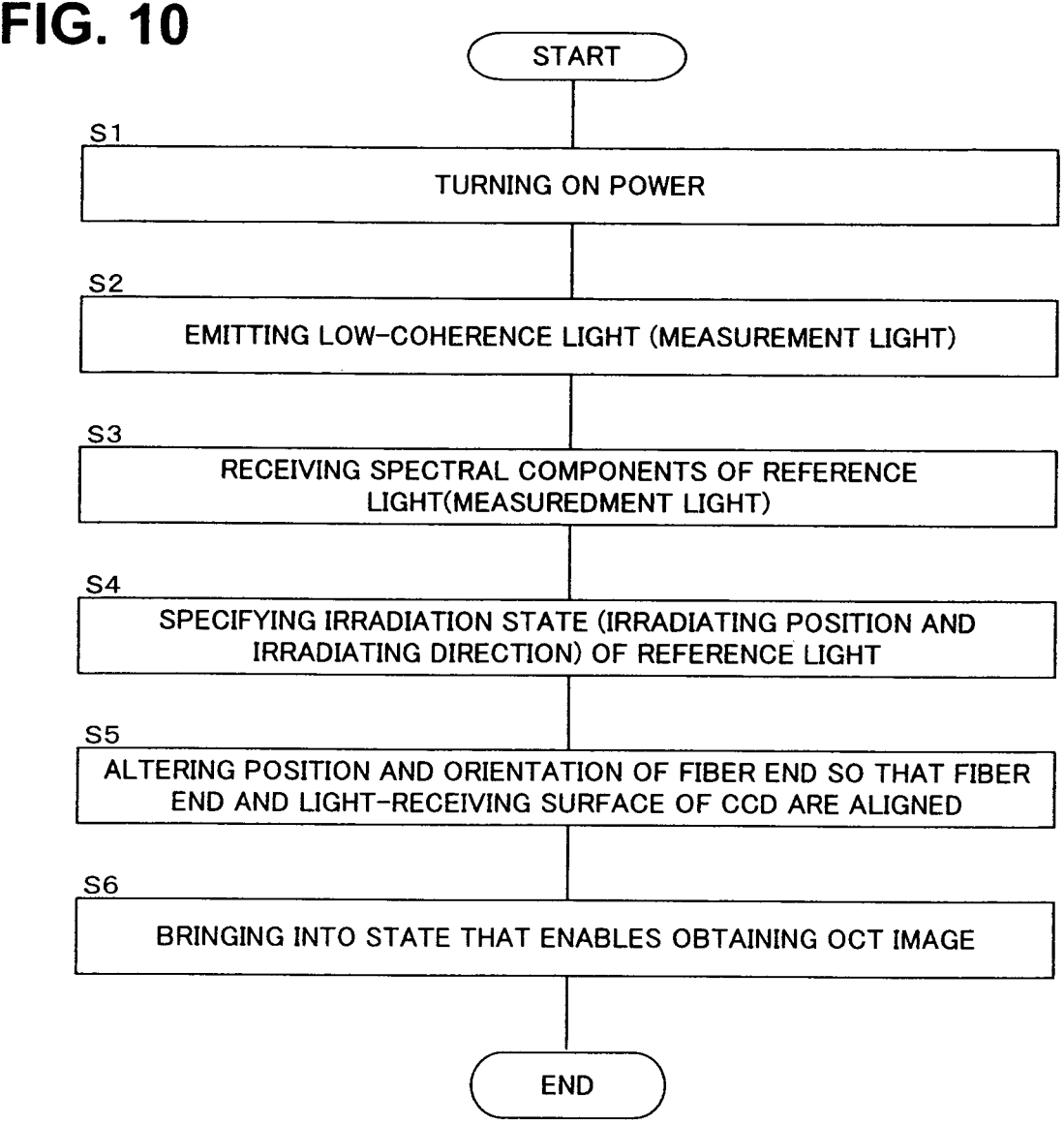
FIG. 10 is a flowchart showing one example of a usage pattern in the preferred embodiment of the device related to the present invention.
Figure 11:
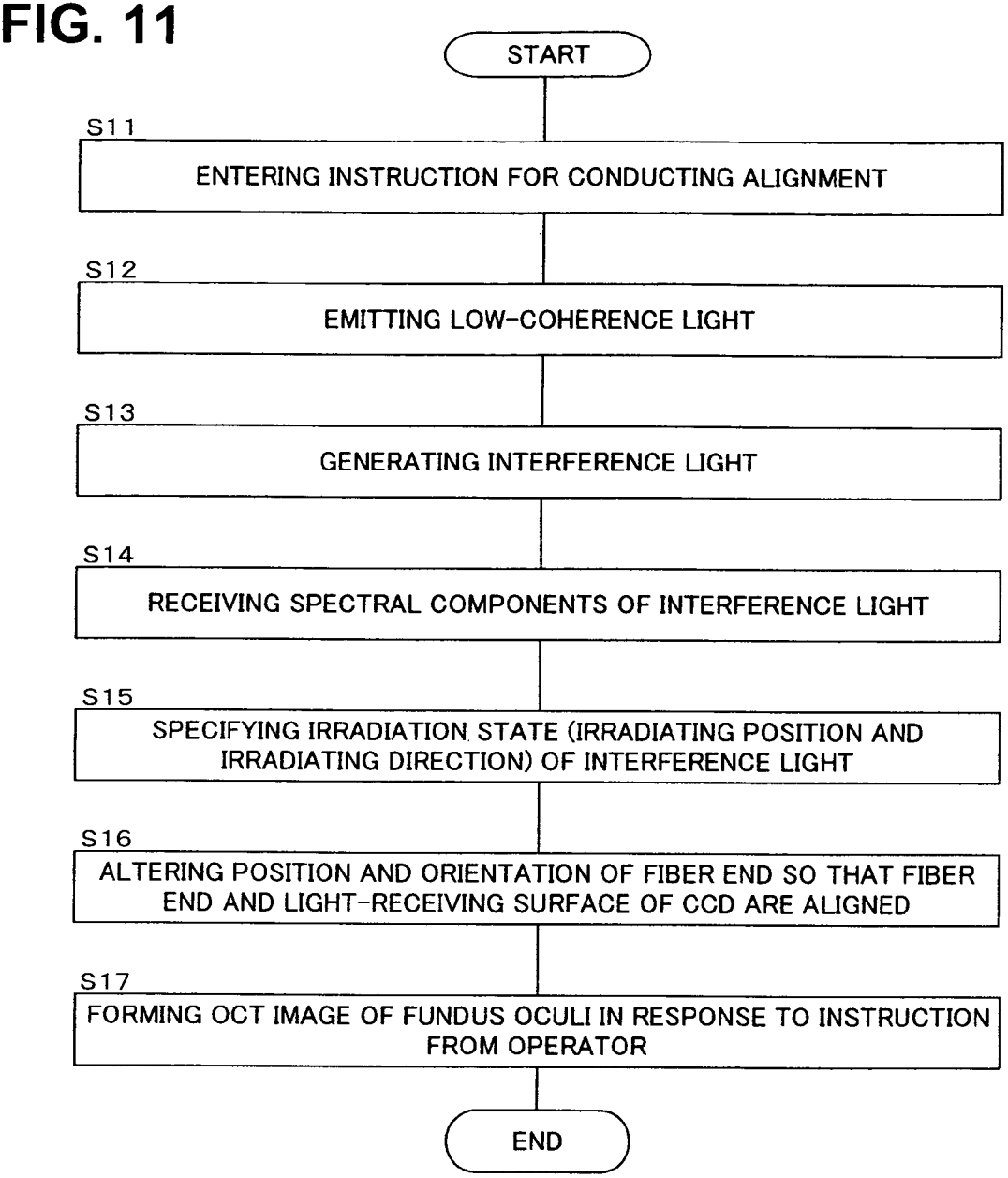
FIG. 11 is a flowchart showing one example of a usage pattern in the preferred embodiment of the device related to the present invention.

Aspects of using the fundus oculi observation device 1 having the configuration above will be explained. Hereinafter, two specific examples of the aspects of using the fundus oculi observation device I will be explained. The flowchart shown in FIG. 10 represents a specific example of the first aspect of usage and the flowchart shown in FIG. 11 represents a specific example of the second aspect of usage.

First Aspect of Usage

The first aspect of usage is intended for the alignment of the fiber end 165a of the optical fiber 165 and the light-receiving surface of the CCD 184 upon turning on the power. First, the operator manipulates the power switch (not shown) to turn on the fundus oculi observation device 1 (S1).

Once the power is turned on, the controller 210 controls the low-coherence light source 160 to emit the low-coherence light L0 (S2). Alternatively, this process may be performed based on instructions from the operator. A portion of the low-coherence light L0 becomes the reference light LR via the optical coupler 162. This reference light LR is employed as the abovementioned measurement light.

The reference light LR goes through the optical fiber 163, the collimator lens 171, the glass block 172, and the concentration filter 173, is reflected by the reference mirror 174, once again goes through the concentration filter 173, the glass block 172, the collimator lens 171, and the optical fiber 163, and returns back to the optical coupler 162. Furthermore, the reference light LR is optically guided by the optical fiber 165 to exit from the fiber end 165a.

The reference light LR that exits the fiber end 165a goes through the collimator lens 181, the diffractive grating 182, and the imaging lens 183, and is irradiated onto the light-receiving surface of the CCD 184. CCD elements on the light-receiving surface of the CCD 184 receive spectral components of the reference light LR that are spectrally resolved by the diffractive grating 182 to obtain (S3). The CCD 184 outputs detection results of the spectral components of the reference light LR (detection signals) to the arithmetic and control device 200.

The irradiation state specifying part 211 analyzes the detection signals input from the CCD 184 to specify the irradiation state of the reference light LR (measurement light) onto the light-receiving surface of the CCD 184 (S4). As a result, the irradiating position and irradiating direction of the reference light LR onto the light-receiving surface of the CCD 184 are specified.

The controller 210 controls the fiber end driving mechanism 244 based on the specified irradiation state of the reference light LR (irradiating position and irradiating direction), and alters the position and orientation of the fiber end 165a so that the reference light LR is properly irradiated onto the light-receiving surface of the CCD 184 (S 5).

Due to the above process, the device is brought into a state that enables the obtaining of an OCT image (S6). As a result, in response to the operator entering an instruction for obtaining an OCT image, the fundus oculi observation device 1 receives the instruction and performs operations for forming an OCT image.

Second Aspect of Usage

The second aspect of usage is intended for the alignment of the fiber end 165a of the optical fiber 165 and the light-receiving surface of the CCD 184 upon obtaining an OCT image. It is assumed that the eye to be examined E is disposed at a predetermined measurement position (position shown in FIG. 1).

First, the operator manipulates the manipulation part 240B and enters an instruction for conducting alignment between the fiber end 165a and the light-receiving surface (S11).

The controller 210 that received this instruction controls the low-coherence light source 160 to emit the low-coherence light L0 (S12).

The low-coherence light L0 is divided into a signal light LS and a reference light LR by the optical coupler 162. The signal light LS is irradiated onto the fundus oculi through the above-mentioned route. The reflected light on the fundus oculi of the signal light LS passes through the same route in the reverse direction and returns back to the optical coupler 162. Meanwhile, the reference light LR returns back to the optical coupler 162 through the same route as that in the first aspect of usage. The optical coupler 162 generates an interference light LC by superimposing the signal light LS and the reference light LR (S13). The interference light LC is optically guided by the optical fiber 165 to exit from the fiber end 165a. The interference light LC is employed as the abovementioned measurement light.

The interference light LC that exits the fiber end 165a goes through the collimator lens 181, the diffractive grating 182, and the imaging lens 183, and is irradiated onto the light-receiving surface of the CCD 184. CCD elements on the light-receiving surface of the CCD 184 receive spectral components of the interference light LC that are spectrally resolved by the diffractive grating 182 (S14). The CCD 184 outputs the detection results of the spectral components of the reference light LR (detection signals) to the arithmetic and control device 200.

The irradiation state specifying part 211 analyzes the detection signals entered from the CCD 184 to specify the irradiation state of the interference light LC (measurement light) onto the light-receiving surface of the CCD 184 (S15). As a result, the irradiating position and irradiating direction of the interference light LC onto the light-receiving surface of the CCD 184 are specified.

The controller 210 controls the fiber end driving mechanism 244 based on the specified irradiation state of the interference light LC (irradiating position and irradiating direction), and alters the position and orientation of the fiber end 165a so that the interference light LC is properly irradiated onto the light-receiving surface of the CCD 184 (S16).

Due to the above process, the device is brought into a state that enables the obtaining of an OCT image of the fundus oculi Ef. In other words, when an operator enters an instruction for obtaining an OCT image, the fundus oculi observation device 1 receives this instruction and performs operations for forming an OCT image of the fundus oculi Ef (S17).

ADVANTAGEOUS EFFECTS

Actions and advantageous effects of the fundus oculi observation device 1 as described above will be described below.

The fundus oculi observation device 1 is used as an optical image measuring device capable of measuring OCT images such as tomographic images of the fundus oculi Ef. The fundus oculi observation device 1 comprises an irradiation state specifying part 211 that specifies the irradiation state of measurement light onto the light-receiving surface of the CCD 184 by specifying the irradiation state (irradiating position and irradiating direction) of measurement light onto the light-receiving surface of the CCD 184.

Furthermore, the fundus oculi observation device 1 comprises a fiber end driving mechanism 244 that alters the position and orientation of the fiber end 165a of the optical fiber 165 based on the irradiation state of measurement light specified by the irradiation state specifying part 211, and is thereby adapted to alter the relative position and orientation between the fiber end 165a of the optical fiber 165 and the light-receiving surface of the CCD 184.

With this fundus oculi observation device 1, it is possible to automatically allow the relative position and orientation between the fiber end 165a of the optical fiber 165 and the light-receiving surface of the CCD 184 to be in a proper positional relationship, thereby making it possible to easily carry out adjustment of the positional relationship between them. By conducting measurement of the fundus oculi Ef after disposing the fiber end 165a and the light-receiving surface in the proper positional relationship, the interference light LC can be received in a state in which the fiber end 165a and the light-receiving surface are properly disposed.

According to the first aspect of usage described above, the positional relationship between the fiber end 165a and the CCD 184 can be automatically adjusted upon the power of the device being turned on, so it is possible to preferably carry out the subsequent measurement of an OCT image. In other words, because the measurement can be carried out in the state in which the fiber end 165a and the CCD 184 are disposed in a proper positional relationship, it is possible to obtain favorable OCT images.

In addition, even when the positional relationship between the fiber end 165a and the CCD 184 becomes unfavorable due to changes in the environmental conditions while not using the fundus oculi observation device 1 (such as nighttime), the positional relationship can be conveniently corrected upon turning on the power.

Meanwhile, according to the second aspect of usage described above, the positional relationship between the fiber end 165a and the CCD 184 can be adjusted, for example, every time the eye to be examined E is changed or at predetermined time intervals, so it is possible to maintain the proper positional relationship between the fiber end 165a and the CCD 184. In particular, even when there is a change in the environmental conditions using the fundus oculi observation device 1, it is possible to maintain the positional relationship between them in a proper state.

MODIFIED EXAMPLES

The configuration explained above is just an example for preferably implementing the optical image measuring device according to the present invention. Therefore, optional modifications within the scope of the invention can be applied accordingly. Hereinafter, various types of modified examples will be explained.

In the abovementioned embodiments, adjustment of the exit position of the interference light from the light guiding part and the position of the light-receiving surface of the light-receiving part is conducted, upon turning on the power of the device or before obtaining an OCT image. On the other hand, this alignment can be carried out at any timing. At that time, it may be configured to perform the alignment in response to an instruction from the operator, or may be configured to automatically perform the alignment. In the latter case, for example, the alignment can be automatically performed at a predetermined time. Moreover, it is desirable that it be configured so as not to carry out the automatic alignment when actually using this device, such as when obtaining an OCT image.

In the above embodiment, the exit position of the light guiding part is altered in order to adjust the exit position of the interference light from the light guiding part and the position of the light-receiving surface of the light-receiving part. Alternatively, it is also possible to configure so as to alter the position of the light-receiving surface of the light-receiving part.

Figure 12:
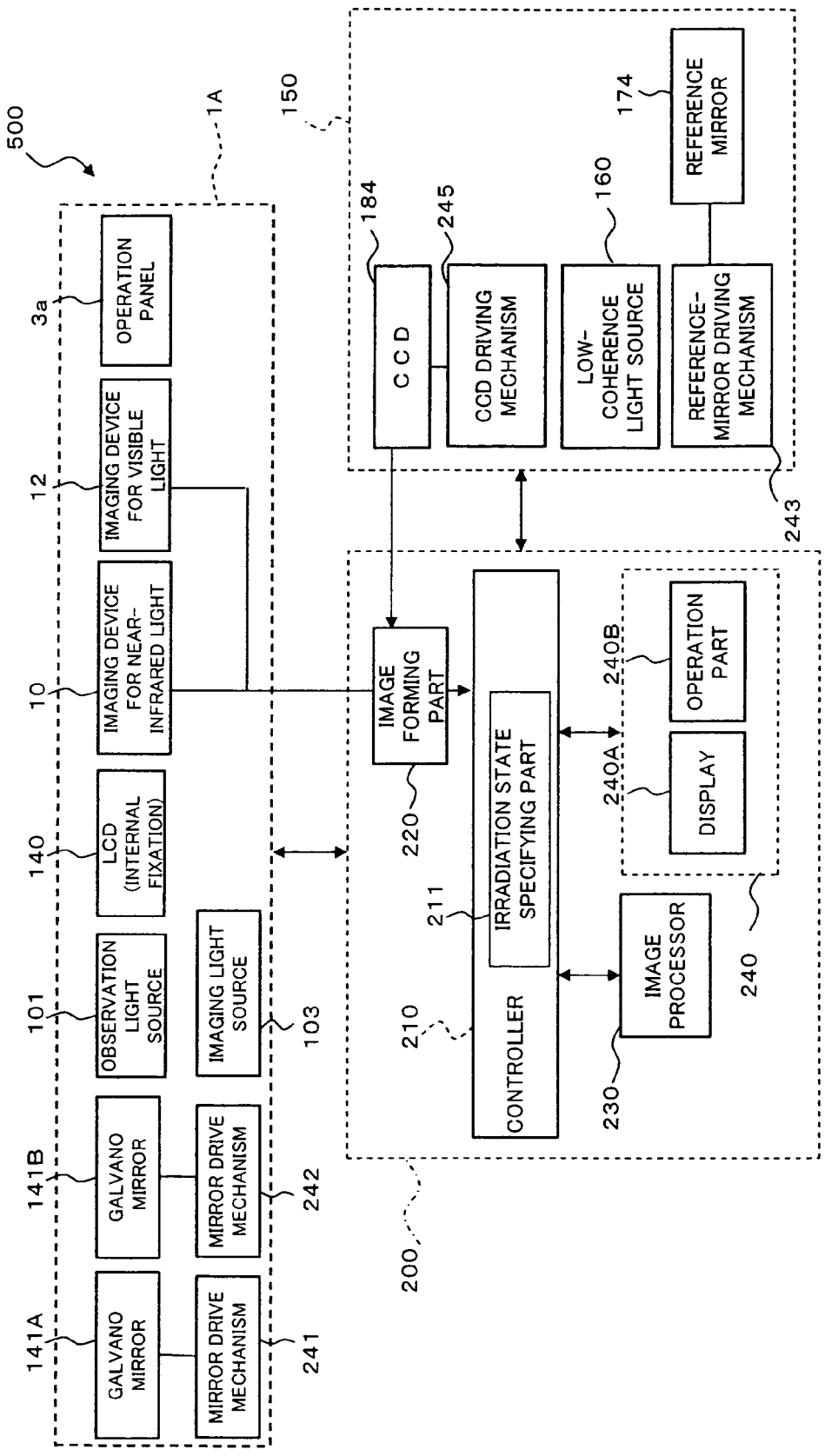
FIG. 12 is a schematic block diagram showing one example of the configuration of a control system in the modified embodiment of the device related to the present invention.
Figure 13:
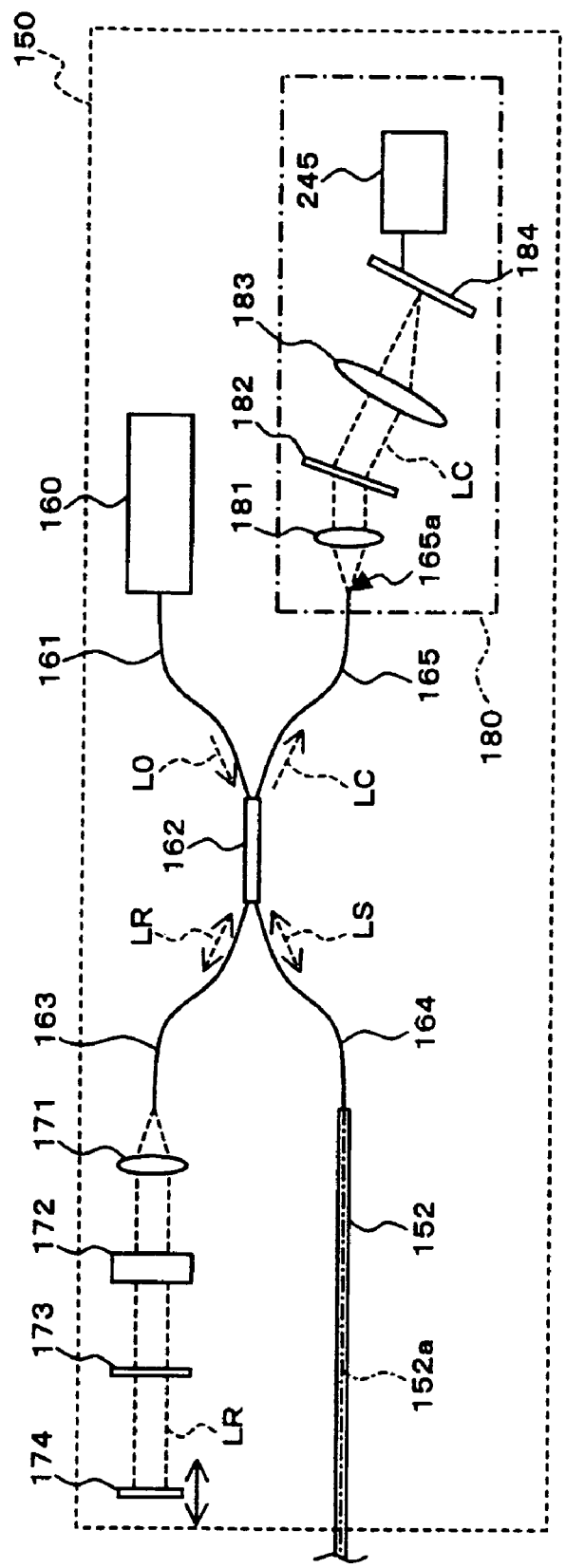
FIG. 13 is a schematic configuration diagram showing one example of the configuration of an OCT unit in the modified embodiment of the device related to the present invention.

FIG. 12 and FIG. 13 represent an example of the configuration of the fundus oculi observation device 500 (optical image measuring device) comprising a function for altering the position of the light-receiving surface of the light-receiving part (CCD). The fundus oculi observation device 500 is configured similarly to the fundus oculi observation device 1 in the above embodiment. In this regard, however, the fundus oculi observation device 500 comprises a CCD driving mechanism 245 instead of the fiber end driving mechanism 244.

The CCD driving mechanism 245 moves the CCD 184 in a direction parallel to the light-receiving surface on which a plurality of CCD elements are arrayed (direction perpendicular to the normal line direction of the light-receiving surface) and in a direction perpendicular to the light-receiving surface (the normal line direction of the light-receiving surface). As a result, the CCD 184 is three-dimensionally moved in a state with the orientation of the light-receiving surface fixed. Furthermore, the CCD driving mechanism 245 moves the CCD 184 so as to alter the orientation of the light-receiving surface (the normal line direction of the light-receiving surface). This operation can be carried out, for example, by attempting to rotate the CCD 184 in a predetermined axial direction (e.g. the normal line direction of the light-receiving surface).

The CCD driving mechanism 245 is configured to include, for example, an actuator such as a stepping motor and a transmission mechanism that transmits driving force output from this actuator. This transmission mechanism is connected to a site other than the light-receiving surface of the CCD 184 such as a rear part or a side part of the CCD 184 (cf. FIG. 13), and is adapted to transmit driving force output by the actuator to the CCD 184.

Herein, it is also possible to separately provide an actuator that outputs driving force for three-dimensionally moving the CCD 184 and an actuator that outputs driving force for altering the orientation of the light-receiving surface, or the three-dimensional movement and the movement for altering the operation of the light-receiving surface may be realized by transmitting driving force output by a single actuator with separate transmission mechanisms. Alternatively, for the three-dimensional movement, separate actuators for moving in each direction may be provided, or the movement in each direction may be realized by transmitting driving force from a single actuator with separate transmission mechanisms. Similarly, also for the altering of the orientation of the light-receiving surface, individual actuators may be provided for each direction in which the orientation alters, or the orientation of the light-receiving surface may be altered in each direction by transmitting driving force from a single actuator with separate transmission mechanisms.

The irradiation state specifying part 211 specifies the irradiation state (irradiating position and irradiating direction) of the interference light LC (measurement light) onto the light-receiving surface of the CCD 184 in a similar manner to the above embodiment. The controller 210 controls the CCD driving mechanism 245 in the same fashion as the fiber end driving mechanism 244 in the above embodiment. As a result, it is possible to automatically adjust the positional relationship between the fiber end 165a of the optical fiber 165 and the light-receiving surface of the CCD 184.

Moreover, it is also possible to configure so as to alter both the exit position of the interference light from the light guiding part and the position of the light-receiving surface of the light-receiving part. As a specific example thereof, it is possible to apply a configuration in which both of the abovementioned fiber end driving mechanism 244 and the CCD driving mechanism 245 are provided. In this case, it is controlled such that the total of the moving distance of the fiber end 165a by the fiber end driving mechanism 244 and the moving distance of the light-receiving surface of the CCD 184 by the CCD driving mechanism 245 will be the moving distance intended for alignment. In addition, it is controlled such that the total of the altering angle of the orientation of the fiber end 165a by the fiber end driving mechanism 244 and the altering angle of the light-receiving surface of the CCD 184 by the CCD driving mechanism 245 will be the altering angle intended for alignment.

In the above embodiment, alignment is carried out by comparing the light-receiving amount of measurement light with a proper value, but it is also possible to apply a configuration in which alignment is carried out only when the light-receiving amount of measurement light is not included within an allowable range. For that purpose, an allowable range of the light-receiving amount of measurement light is provided in advance. This allowable range is set as the range in which an OCT image that is formed based on the detection results of the interference light LC in this condition is allowable, such as the light-receiving amount of the spectral components of measurement light being 80% or more of the abovementioned proper value. This allowable range is stored on, for example, a hard disk drive 204 (irradiation state specifying part 211).

The irradiation state specifying part 211 specifies the light-receiving amount of measurement light based on the detection signal from the CCD 184 that has received measurement light, and determines whether the specified light-receiving amount is included in the allowable range. When the light-receiving amount is determined to be included in the allowable range, the controller 210 does not conduct adjustment of the positional relationship between the fiber end 165a and the CCD 184. On the other hand, when the light-receiving amount is determined not to be included in the allowable range, the controller 210 controls the fiber end driving mechanism 244 and/or the CCD driving mechanism 245 to alter the positional relationship between the fiber end 165a and the CCD 184.

According to this modified example, when the light-receiving amount of measurement light is within the allowable range, that is, when the light-receiving amount of the interference light LC is within the allowable range, there is a merit in that, because it acts so as not to conduct adjustment of the positional relationship between the fiber end 165a and the CCD 184, unnecessary adjustment operations are not carried out.

In addition, it is also possible to configure so as to output notifying information when the light-receiving amount of measurement light is determined not to be included within the allowable range. As this notifying information, included is visual information such as character string information or image information that indicates that the light-receiving amount of measurement light is outside the allowable range (that a favorable OCT image cannot be obtained), auditory information such as a beep sound, and the like. The visual information is displayed on the displaying part 240A by the controller 210, for example. Moreover, it may be visually notified by providing a light source such as an LED on a visual part of the device and lighting or blinking this light source. In addition, auditory information is output by a not-shown audio output part (such as an amplifier and a speaker). The displaying part 240A, the LED, or the audio output part that outputs the notifying information in this way is equivalent to an example of the "notifying part" of the present invention. Moreover, in each case, the output operation of the notifying information is controlled by the controller 210.

The light-receiving part according to the present invention is not limited to the line sensor on which a plurality of light detection elements are one-dimensionally arrayed. For example, it is possible to employ, as the light-receiving part, a sensor having two or more lines, that is, a sensor on which a plurality of elements are two-dimensionally arrayed.

In this case, it is possible to specify which element has detected a light, so based on the specified result, it is possible to alter the relative position of the exit end of light from the light guiding part and the light-receiving part so as to allow a predetermined element to detect a light.

For example, when the light-receiving part has odd-numbered lines, an element on the middle line is assumed to be the abovementioned predetermined element. Once the light-receiving part has received light, an element that has received the light is specified at this time.

When the element on the middle line receives light, the positional relationship between the exit end and the light-receiving part in a perpendicular direction of lines is proper. Moreover, for the relative position in a direction along the lines, alignment can be carried out in a similar manner to the above embodiment.

Meanwhile, when an element other than that on the middle line receives light, the distance between the element that has received the light and the middle line is calculated. This calculation process can be easily carried out, for example, based on the interval between adjacent lines (known). In addition, it is also possible to specify the direction of the element that has received light onto the middle line. Altering the relative position of the exit end and the light-receiving part based on the distance and direction obtained in this way allows a predetermined element of the light-receiving part to receive light. Moreover, for the relative position in a direction along the lines, the alignment can be carried out in a similar manner to the above embodiment.

Moreover, when the light-receiving part has even-numbered lines, a similar process to that in the case of odd-numbered lines can be performed by, for example, assuming an element on one and/or both of the middle two lines to be the predetermined element.

Alternatively, it is also possible to improve the detection sensitivity by binning (a technique for amplifying the signal by lumping together a plurality of adjacent pixels to virtually enlarge the light-receiving area and for detecting the same). In addition, it is possible to specify how one light is divided and detected in a plurality of pixels. As a result, compared to the case in which relative errors between the exit end of light and the light-receiving part are specified using an interval between pixels as a unit, it is possible to more precisely specify relative errors.

Figure 14:
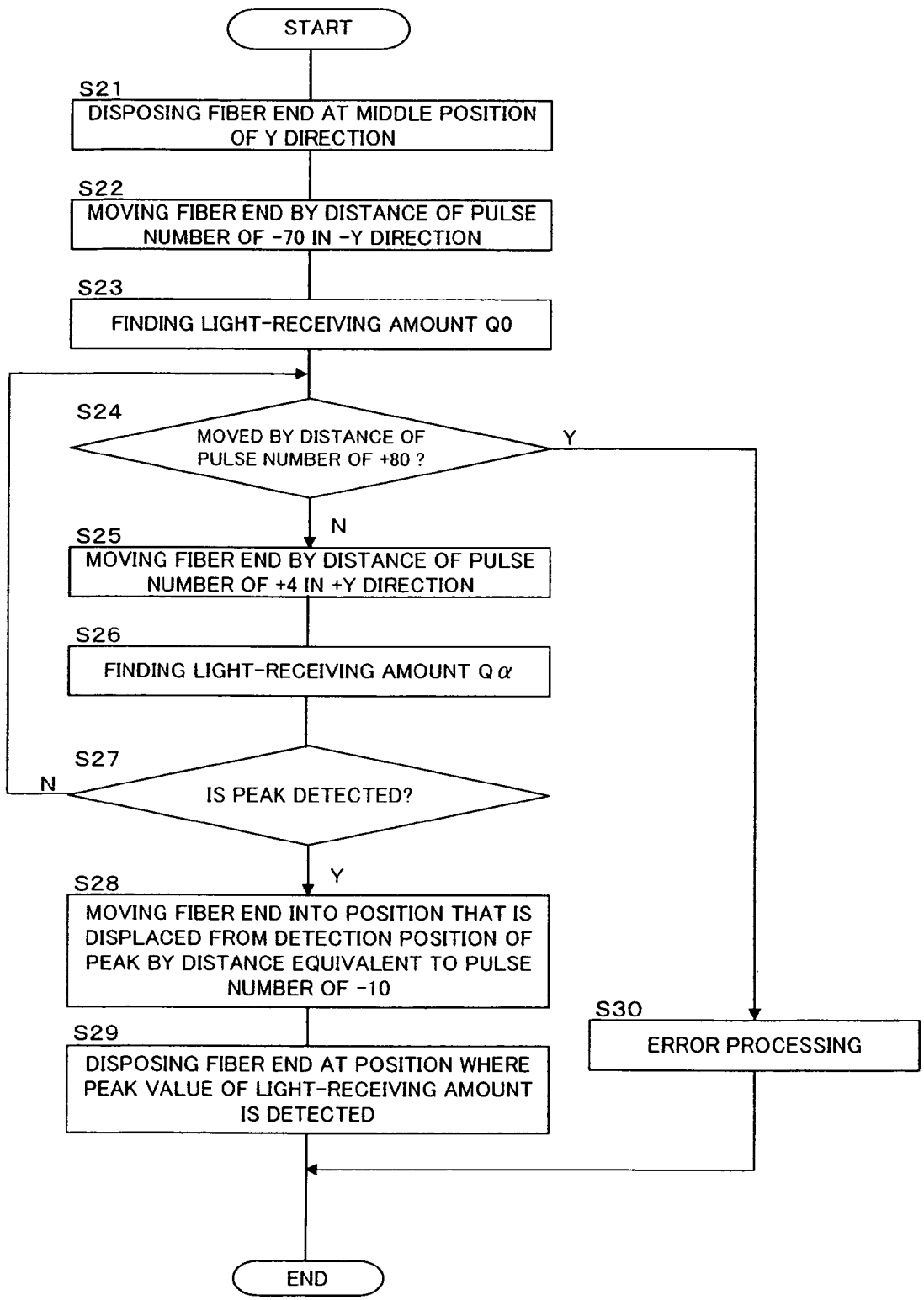
FIG. 14 is a flowchart showing one example of a usage pattern in the modification of the device related to the present invention.
Figure 15:
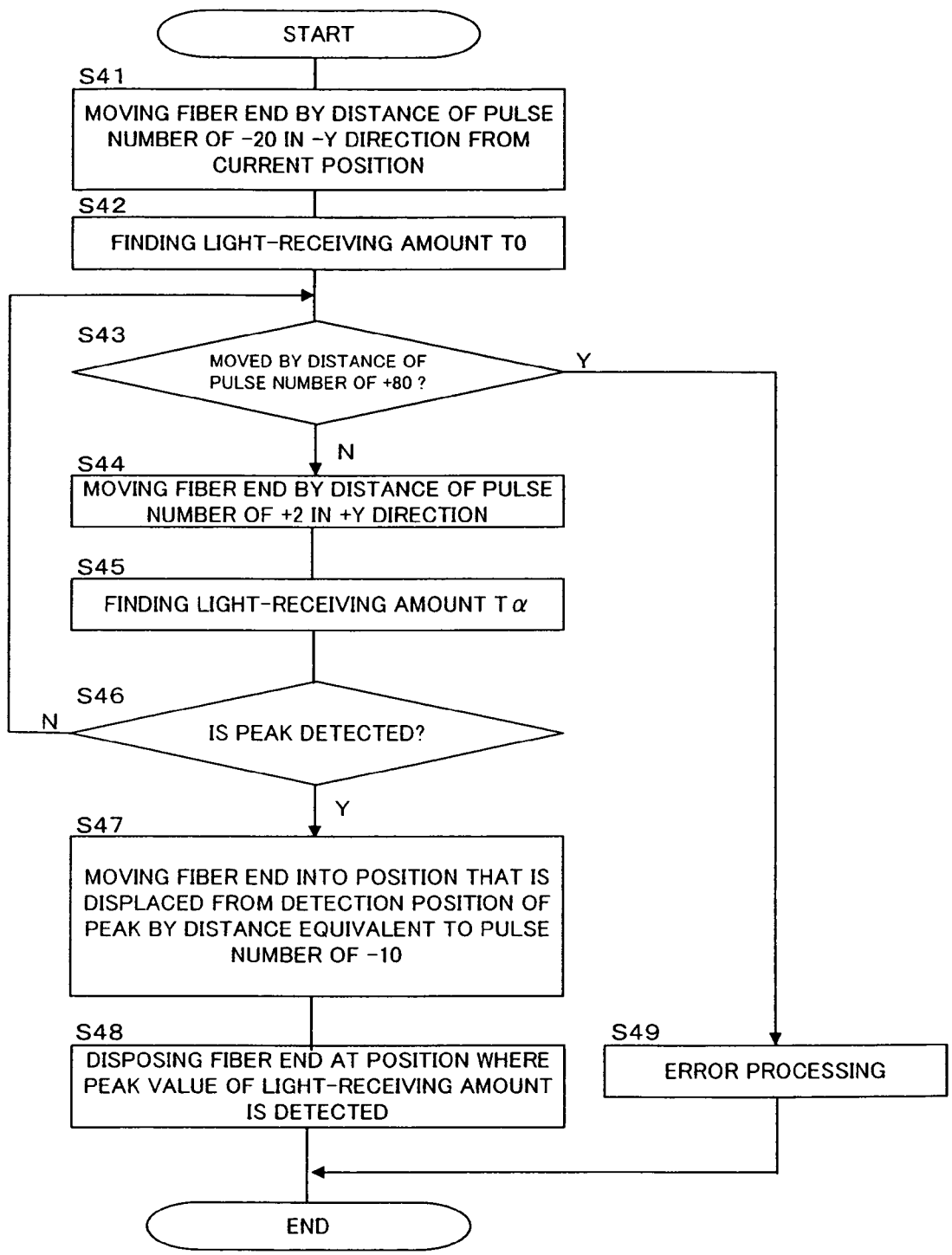
FIG. 15 is a flowchart showing one example of a usage pattern in the modification of the device related to the present invention.

In addition, with the processes shown in FIG. 14 and FIG. 15, it is also possible to carry out alignment between the fiber end 165a of the optical fiber 165 and the light-receiving surface of the CCD 184. The process shown in FIG. 14 is an example of rough adjustment of the relative position of the fiber end 165a and the light-receiving surface. In addition, the process shown in FIG. 15 is an example of fine adjustment of the relative position of the fiber end 165a and the light-receiving surface.

The rough adjustment shown in FIG. 14 will be explained. Rough adjustment is employed for alignment in the spread direction of spectral components of the interference light LC that has been dispersed by the diffractive grating 182. This direction is referred to as the dispersion direction.

The CCD 184 is assumed to be a line sensor on which a plurality of CCD elements are arrayed along the dispersion direction. In addition, the actuator of the fiber end driving mechanism 244 (or CCD driving mechanism 245: similar hereinafter) is assumed to be a stepping motor (pulse motor).

Furthermore, the pulse number necessary to move the irradiating position of spectral components of the interference light LC onto the light-receiving area of the CCD 184 by a distance of half the array of the plurality of CCD elements is assumed to be 70.

In addition, assume that the pulse number of pulse signals for moving the irradiating position of spectral components in the positive direction of the dispersion direction (e.g. upward direction: +y direction) is represented by a positive sign (+) and the pulse number of pulse signals for moving the same in the negative direction (e.g. downward direction: −y direction) is represented by a negative sign (−).

Once the initiation requirement of rough adjustment is instructed, the controller 210 sends a pulse signal to the fiber end driving mechanism 244 and disposes the fiber end 165a at the middle position of the moving range in the y direction (S21).

This process can be carried out, for example, by detecting the position of the fiber end 165a (the rotational position of the stepping motor), finding the difference between this detection position and the middle position, generating a pulse signal with the pulse number equivalent to this difference, and sending the same to the fiber end driving mechanism 244.

Next, the controller 210 sends a pulse signal with a pulse number of −70 to the fiber end driving mechanism 244. Upon receiving this pulse signal, the fiber end driving mechanism 244 moves the fiber end 165a by a distance of half the array of CCD elements in the −y direction (S22). As a result, the irradiating position of spectral components is moved to (the proximity of) the end in the −y direction.

Then, the controller 210 controls the low-coherence light source 160 to emit the low-coherence light L0. The CCD 184 receives spectral components of measurement light (interference light LC or reference light LR) based on this low-coherence light L0. The irradiation state specifying part 211 finds the light-receiving amount Q0 based on this light-receiving result (S23). The value of the light-receiving amount (initial value) Q0 is stored on the RAM 202 or the hard disk drive 204.

Next, the controller 210 sends a pulse signal with a predetermined positive pulse number (e.g. +4) to the fiber end driving mechanism 244. Upon receiving this pulse signal, the fiber end driving mechanism 244 moves the fiber end 165a by a distance equivalent to the pulse number of +4 in the +y direction (S25).

The controller 210 controls the low-coherence light source 160 to emit the low-coherence light L0. The CCD 184 receives spectral components of measurement light based on this low-coherence light L0. The irradiation state specifying part 211 finds the light-receiving amount Q1 based on this light-receiving result (S26).

The irradiation state specifying part 211 detects the peak of the light-receiving amount (S27). In the phase in which the first light-receiving amount Q1 has been obtained, the peak is not detected (S27: N).

In this phase, the fiber end 165a has not yet moved by a distance equivalent to the pulse number of +80 (S24: N), so the controller 210 sends a pulse signal with a pulse number of +4 to the fiber end driving mechanism 244 and moves the fiber end 165a by a distance equivalent to the pulse number of +4 in the +y direction (S25).

In this way, steps 24 through 27 are repeated until it is determined to be "Y" at step 27, or until it is determined to be "Y" at step 24.

Moreover, the controller 210 makes this determination at step 24. As a specific example of this process, the controller 210 counts the number of times having sent a pulse signal at step 24 and determines whether this count number has approached 20 (=80 divided by 4) to make a determination at step 24.

A specific example of the process for detecting the peak of the light-receiving amount (S27) will be explained. Assuming that steps 24 through 26 have repeated L times (L=2 to 20), L+1 portions of light-receiving amount $Q\alpha$ ($\alpha$=0, 1, 2, ..., and L) have been obtained by this phase.

At this time, the irradiation state specifying part 211 determines whether the following condition is met: Q(L−2)<Q(L−1) and Q(L−1)>QL. This condition is equivalent to Q(L−1) being the peak of the light-receiving amount. Moreover, the process for detecting the peak is not limited to this, but the peak also can be detected by applying any heretofore known technique.

When the peak value Q(L−1) of the light-receiving amount has been detected (S27: Y), the fiber end 165a is disposed at a position corresponding to the light-receiving amount QL, that is, a position that is moved by a distance equivalent to the pulse number (+4×L) in the +y direction from the position where it is moved at step 22.

The controller 210 controls the fiber end driving mechanism 244 to move the fiber end 165a into a position that is displaced from the detection position of the peak by a distance equivalent to a pulse number of −10 in the −y direction (S28).

More specifically, the controller 210 generates a pulse signal with a pulse number of −14 (=−4−10) and sends the same to the fiber end driving mechanism 244. Upon receiving this pulse signal, the fiber end driving mechanism 244 moves the fiber end 165a by a distance equivalent to the pulse number of −14 in the −y direction. Herein, because the position equivalent to the pulse number of −4 is the detection position of the peak value Q(L−1), the fiber end 165a is moved by this process into a position that is displaced from the detection position of the peak by a distance equivalent to the pulse number of −10.

Furthermore, the controller 210 generates a pulse signal with a pulse number of +10 and sends the same to the fiber end driving mechanism 244. Upon receiving this pulse signal, the fiber end driving mechanism 244 moves the fiber end 165a by a distance equivalent to the pulse number of +10 in the +y direction. As a result, the fiber end 165a is disposed at the position where the peak value Q(L−1) of the light-receiving amount has been detected (S29). This is the end of the process in this case.

Meanwhile, when the fiber end 165a has been moved by a distance equivalent to a pulse number of +80 without the peak of the light-receiving amount being detected (S24: Y), the controller 210 allows the performing of predetermined error processing (S30).

This error processing is, for example, processing as follows. First, the controller 210 allows performing the above processes (S21 through S29) again. Thereby, when the fiber end 165a has been moved again by a distance equivalent to the pulse number of +80 without the peak of the light-receiving amount being detected (S24: Y), the controller 210 controls the displaying part 240A to display predetermined error information.

This error information includes, for example, messages such as "Would you like to try again? Or would you like to quit?", software keys such as a "retry" button and a "quit" button, or the like.

When the "retry" button is clicked, the controller 210 performs the above process again. On the other hand, when the "quit" button is clicked, the controller 210 moves the fiber end 165a into a predetermined position and quits the alignment process. This predetermined position includes, for example, a position prior to conducting step S21, a position after conducting step 21, a position where the light-receiving amount was at a maximum within the above search region, and so on.

Processing can be carried out for moving the fiber end 165a into the position such that the light-receiving amount is at the maximum, for example, as follows. First, the irradiation state specifying part 211 specifies the maximum value QM (M=0 to 20) of 21 portions of the light-receiving amounts Q0 to Q20 that have been obtained by the above process. Next, the controller 210 generates a pulse signal with a pulse number of {−4×(20−M)} and sends the same to the fiber end driving mechanism 244. Upon receiving this pulse signal, the fiber end driving mechanism 244 moves the fiber end 165a into the position where the maximum value QM has been detected.

Moreover, in the aspect of usage explained herein, when the peak is detected, instead of directly moving the fiber end 165a to the peak detection position, it is adapted to move the same to pass through the peak detection position, into a position away by a predetermined distance (a distance equivalent to the pulse number of +10) once (S28), and further move the same into the peak detection position (S29). This operation is intended to eliminate errors in the moving distance resulting from the rotation direction of the stepping motor. Moreover, it is also possible to configure so as to move the fiber 165a into the peak detection position when the peak is detected. This is the end of the explanation of rough adjustment.

Next, fine adjustment will be explained with reference to FIG. 15. Fine adjustment is employed for alignment in the dispersion direction, as is the case with the abovementioned rough adjustment.

Once the initiation requirement for fine adjustment is instructed, the controller 210 generates a pulse signal with a pulse number of −20, sends the same to the fiber end driving mechanism 244, and moves the fiber end 165a by a distance equivalent to the pulse number of −20 in the −y direction from the current position (S41).

Next, the controller 210 controls the low-coherence light source 160 to emit the low-coherence light L0. The CCD 184 receives spectral components of measurement light based on this low-coherence light L0. The irradiation state specifying part 211 determines the light-receiving amount TO based on this light-receiving result (S42). The value of the light-receiving amount (initial value) TO is stored on the RAM 202 or the hard disk drive 204.

Next, the controller 210 sends a pulse signal with a predetermined positive pulse number (e.g. +2: less than rough adjustment) to the fiber end driving mechanism 244. Upon receiving this pulse signal, the fiber end driving mechanism 244 moves the fiber end 165a by a distance equivalent to a pulse number of +2 in the +y direction (S44).

The controller 210 controls the low-coherence light source 160 to emit the low-coherence light L0. The CCD 184 receives spectral components of measurement light based on this low-coherence light L0. The irradiation state specifying part 211 finds the light-receiving amount TI based on this light-receiving result (S45).

The irradiation state specifying part 211 detects the peak of the light-receiving amount, for example, in a similar manner to the case of rough adjustment (S46). In the phase in which the first light-receiving amount TI has been obtained, the peak is not detected (S46: N).

In this phase, the fiber end 165a has not yet moved by a distance equivalent to a pulse number of +80 (S43: N), so the controller 210 sends a pulse signal with a pulse number of +2 to the fiber end driving mechanism 244 and moves the fiber end 165a by a distance equivalent to the pulse number of +2 in the +y direction (S44).

In this way, steps 43 through 46 are repeated until it is determined to be "Y" at step 46, or until it is determined to be "Y" at step 43.

When the peak value T(L−1) of the light-receiving amount has been detected (S46: Y), the controller 210 controls the fiber end driving mechanism 244 to move the fiber end 165a into a position that is displaced from the detection position of the peak by a distance equivalent to a pulse number of −10 in the −y direction (S47).

Furthermore, the controller 210 generates a pulse signal with a pulse number of +10, sends the same to the fiber end driving mechanism 244, and moves the fiber end 165a by a distance equivalent to the pulse number of +10 in the +y direction. As a result, the fiber end 165a is disposed at the position where the peak value T(L−1) of the light-receiving amount has been detected (S48). This is the end of the process in this case.

On the other hand, when the fiber end 165a has been moved by a distance equivalent to a pulse number of +80 without the peak of the light-receiving amount being detected (S43: Y), the controller 210 allows the performing of predetermined error processing (S49). This error processing is similar to the case of rough adjustment, for example. This is the end of the explanation of fine adjustment.

Figure 16:
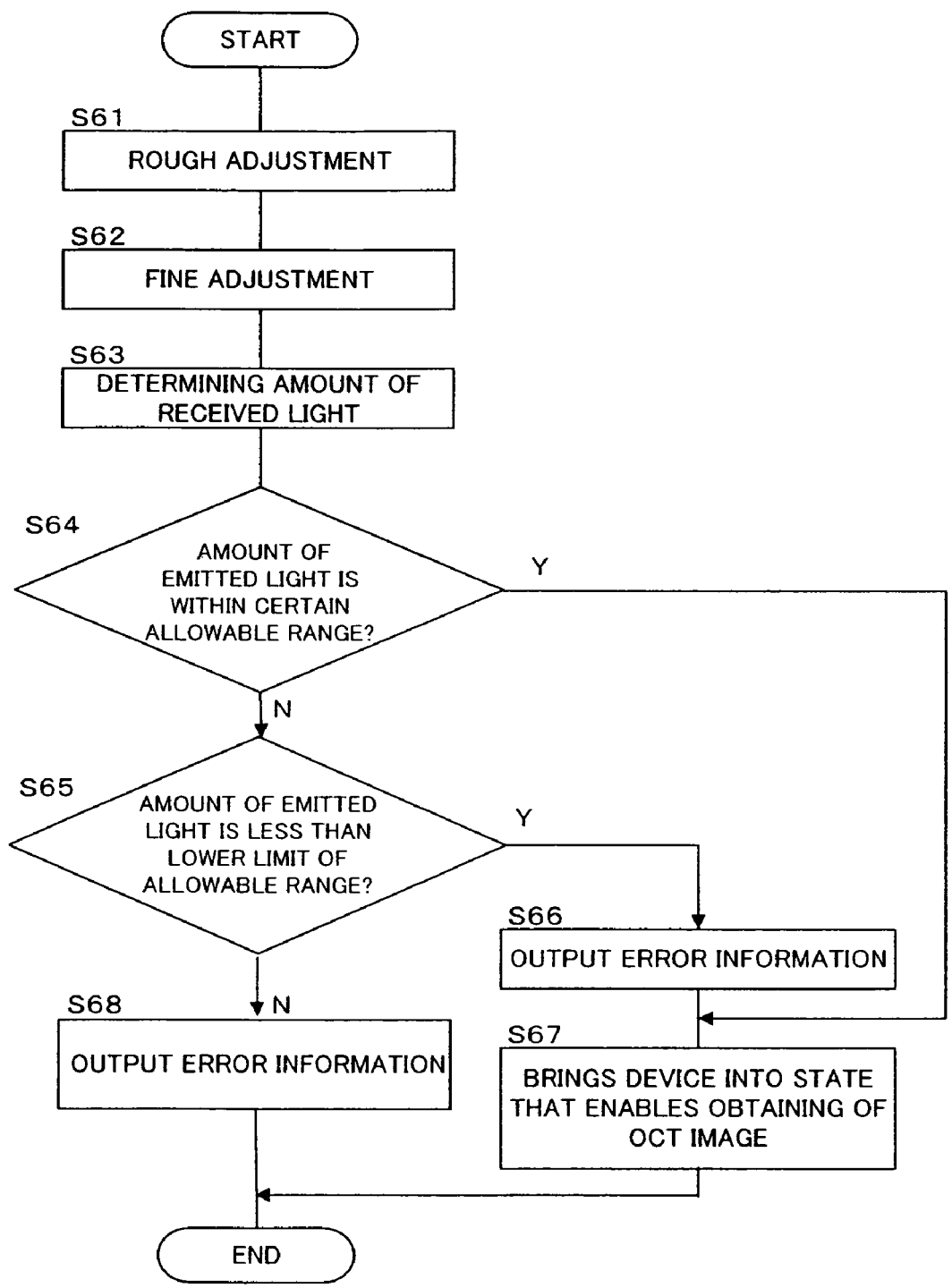
FIG. 16 is a flowchart showing one example of a usage pattern in the modification of the device related to the present invention.
Figure 17:
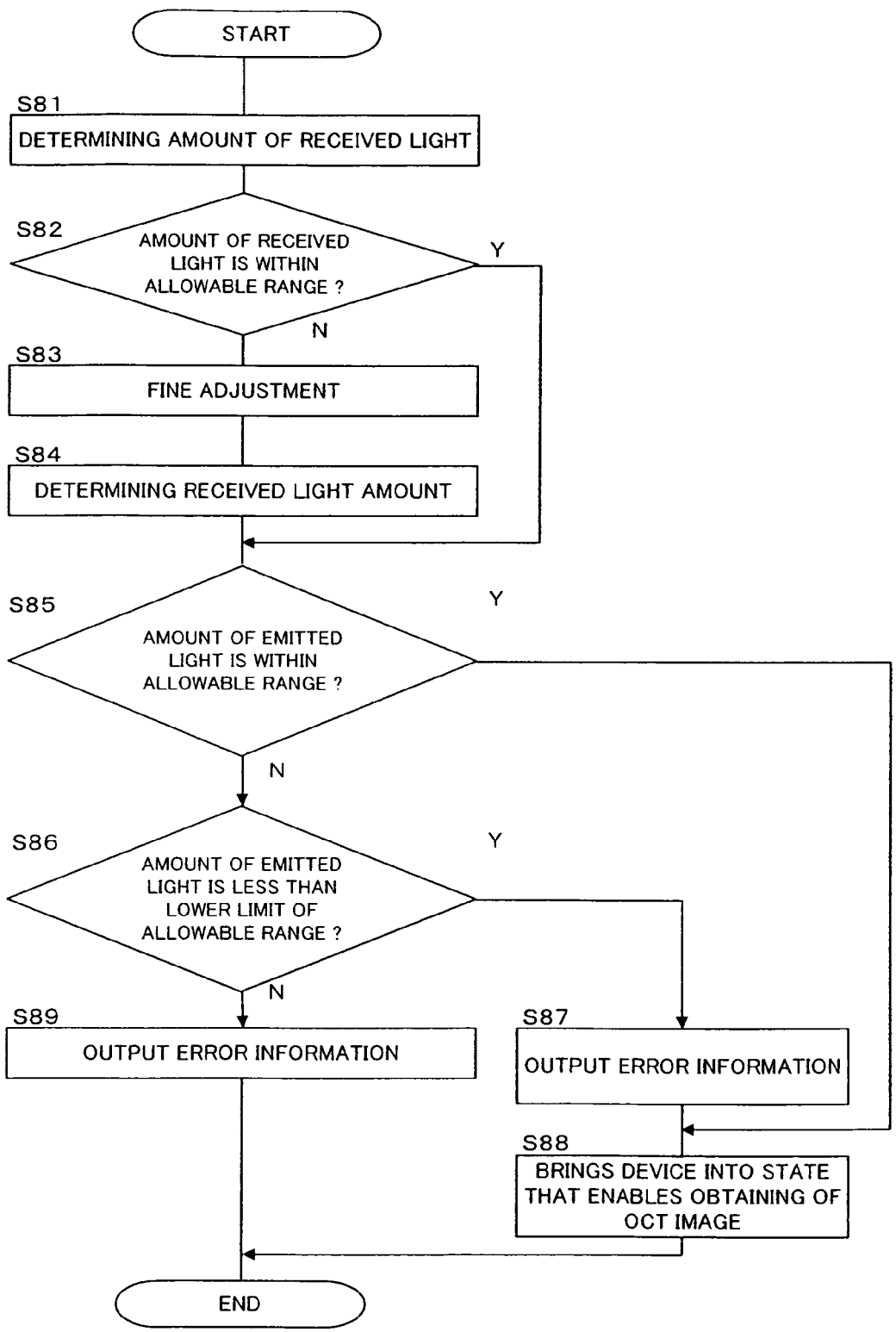
FIG. 17 is a flowchart showing one example of a usage pattern in the modification of the device related to the present invention.

Referring to FIG. 16 and FIG. 17, one example of the embodiment that utilizes rough adjustment and fine adjustment is explained below.

The processing shown in FIG. 16 is performed, for example, when the device is turned on or when the subject eyes are first examined after power-on.

First of all, the controller 210 brings the rough adjustment (S61) and fine adjustment (S62) into practice. After fine adjustment is completed, the controller 210 controls the low-coherence light source 160 to emit low-coherence light L0. CCD 184 receives spectral components of the measurement light based on this low-coherence light L0. The irradiation state specifying part 211 determines an amount of received light based on this result of receiving light (S63).

Furthermore, the irradiation state specifying part 211 determines whether or not the amount of received light is included within a certain allowable range (S64).

The amount of received light is detected in order to determine the appropriateness of the amount of low-coherence light L0 (amount of emitted light) that is emitted from the low-coherence light source 160. Therefore, the allowable range is preliminarily set for the amount of emitted light from the low-coherence light source 160.

Herein, the light amount received by CCD 184 is influenced by both the amount of emitted light from the low-coherence light source 160 and the positional relationship between the fiber end 165*a* and the light-receiving surface. In this embodiment, since rough adjustment and fine adjustment have already been performed, it is considered that the fiber end 165*a* and the light-receiving surface are arranged in an (substantially) appropriate positional relationship. Therefore, based on this assumption, the amount of emitted light can be obtained from the received light amount. Considering errors in the positional relationship, it is also possible to set the allowable range in Step 64 to be slightly broad.

In addition, the allowable range of the amount of emitted light may be set based on the result of fine adjustment (S62). For example, using a ratio of the peak value T (L−1) obtained from fine adjustment to the received light amount in an optimum positional relationship (which can be set in advance, such as at the time of shipping), it can be constituted so as to correct the allowable range of the amount of emitted light in the optimum positional relationship.

When the amount of emitted light is determined to be within the allowable range (S64:Y), the controller 210 brings the device into a state that enables the obtaining of an OCT image, that is, a standby state for a request to obtain an OCT image (S67). In this case, this is the end of the processing.

When the amount of emitted light is outside of the allowable range (S64:N), the irradiation state specifying part 221 determines if the amount of emitted light is less than the lower limit of the allowable range (S65).

When it is determined to be less than the lower limit (S65:Y), the controller 210 controls the display unit 240A to display specific warning information (S66).

This warning information contains, for example, messages including "The light source power is less than the lower limit," or soft keys including the "OK" button, "light amount adjustment" button, etc. When the "OK" button is clicked, the controller 210 brings this device into a state that enables the obtaining of an OCT image (S67). When the "light amount adjustment" button is clicked, the controller 210 controls the display unit 240A to display, for example, a specific operation screen. Then, after the operator completes adjustment of the amount of emitted light, the controller 210 brings this device into a state that enables the obtaining of an OCT image (S67). In this case, this is the end of the processing.

On the other hand, when it is determined that the amount of emitted light is not less than the lower limit but more than the upper limit of the allowable range (S65:N), the controller 210 controls the display unit 240A to display specific error information (S68).

This error information contains, for example, messages including "The light source power exceeds the upper limit." In this case, the "light amount adjustment" button may be displayed to allow for adjustment of the light amount as mentioned above. This is the end of this embodiment.

The processing shown in FIG. 17 is explained below. This processing is performed, for example, when examining the second or later subject eyes. This processing can be performed for each of the subject eyes, at a certain interval, or for a certain number of subject eyes.

Firstly, the controller 210 controls the low-coherence light source 160 to emit the low-coherence light L0. CCD 184 receives spectral components of the measurement light based on this low-coherence light L0. The irradiation state specifying part 211 determines the amount of received light based on this result of receiving light (S81).

Furthermore, the irradiation state specifying part 211 determines whether or not the amount of received light is within a certain allowable range (S82). This allowable range is set in advance to determine whether or not adjustment should be done for the positional relationship between the fiber end 165*a* and the light-receiving surface.

When the received light amount is determined to be within the allowable range (S82:Y), the process moves to the below-mentioned step 85.

On the other hand, when the amount of received light is determined to be outside of the allowable range (S82:N), the controller 210 brings fine adjustment (S83) into practice. After fine adjustment is completed, the controller 210 controls the low-coherence light source 160 to emit the low-coherence light L0. CCD 184 receives spectral components based on this low-coherence light L0. The irradiation state specifying part 211 determines the received light amount based on this result of receiving light (S84). The amount of received light is a result of adjusting the positional relationship between the fiber end 165*a* and the light-receiving surface.

The irradiation state specifying part 211 determines whether or not the amount of received light is within a certain allowable range (S85). Similar to Step 64 in FIG. 16, this amount of received light is detected in order to determine the appropriateness of the amount of emitted light from the low-coherence light source 160.

In addition, the amount of received light for determination in Step 85 refers to the amount of received light obtained in Step 81 when it is determined as "Y" in Step 82, while it refers to the amount of received light obtained in Step 84 when it is determined as "N" in Step 82.

When the amount of emitted light is determined to be within the allowable range (S85:Y), the controller 210 brings the device into a state that enables the obtaining of an OCT image (S88). In this case, this is the end of the processing.

When the amount of emitted light is outside of the allowable range (S85:N), the irradiation state specifying part 221 determines whether the amount of emitted light is less than the lower limit of the allowable range (S86).

When it is determined to be less than the lower limit (S86:Y), similar to Step 66 in FIG. 16, the controller 210 controls the display unit 240A to display specific warning information (S87). For example, receiving a request from the operator, the controller 210 brings this device into a state that enables the obtaining of an OCT image (S88). In this case, this is the end of the processing.

On the other hand, when it is determined to be no less than the lower limit (S86:N), similar to Step 68 in FIG. 16, the controller 210 controls the display unit 240A to display specific error information (S89). This is the end of this embodiment.

According to the above mentioned embodiment, it achieves an automatic search for the relative position of the fiber end 165a and the light-receiving surface such that the amount of received light reaches the peak. Furthermore, it also allows for automatic determination of the amount of emitted light.

However, when the amount of emitted light exceeds the upper limit, it is necessary to discontinue the examination in view of safety to the subject eyes or to conduct the examination after decreasing the amount of emitted light. On the other hand, when the amount of emitted light is less than the lower limit, for example, there is no problem with conducting the examination at the operator's request.

In the above mentioned embodiment, the positional relationship between the fiber end 165a and the light-receiving surface is actually supposed to be altered. Instead of altering the "spatial positional relationship" between the fiber end 165a and the light-receiving surface as mentioned, altering the "optical positional relationship" between the fiber end 165a and the light-receiving surface allows the obtaining of similar effects.

For example, it is possible to alter the optical positional relationship between the fiber end 165a and the light-receiving surface by bending the light path of the interference light LC irradiating from the fiber end 165a (or spectral components after dispersion: hereinafter same as above).

As a concrete example, a prism member is inserted into the light path between the fiber end 165a and the light-receiving surface to bend the light path of the interference light LC, thereby allowing altering of the position of the interference light LC irradiated on the light-receiving surface.

The prism member is inserted/exerted into/from the light path by means of a driving mechanism including an actuator, such as a stepping motor or solenoidal coil.

Further, for example, a variable prism can be used as the prism member. The variable prism is an optical member that can alter the prism value. For example, the controller 210 controls the variable prism to gradually alter the prism value, and thereby gradually alter the irradiation position of the interference light LC to the light-receiving surface, which allows for searching for the above mentioned peak value.

For example, in the embodiment described above, the difference between the light path of a signal light and the light path of a reference light (difference in optical path length) is changed by changing the position of the reference mirror 174, but the method for changing the difference in optical path length is not limited to this. For instance, it is possible to change the difference in optical path length by integrally moving the retinal camera unit 1A and the OCT unit 150 with respect to the eye to be examined and changing the optical path length of the signal light LS. Furthermore, it is also possible to change the difference in optical path length by moving a measurement object in a depth direction (z-direction).

The fundus oculi observation device described in the above embodiment comprises an optical image measurement device of Fourier domain type, but it is also possible to apply the configuration of the present invention to an optical image measurement device of Time Domain type. The time domain type of optical image measurement device is described in, for example, Japanese Unexamined Patent Application Publication 2005-241464. Moreover, it is also possible to apply the configuration of the present invention to an optical image measurement device of any other type such as a Swept Source type.

In the above mentioned embodiment, a device for obtaining an OCT image of the fundus has been explained. However, the composition of the abovementioned embodiment can be applied to a device that is capable of obtaining an OCT image of other sites in the subject eyes, such as the cornea. In addition, the composition of the abovementioned embodiment can be also applied to a device that is capable of obtaining an OCT image of any object to be measured (subject in other medical, biological, and industrial fields), for which an image can be obtained by OCT technology.

What is claimed is:

1. An optical image measuring device comprising:
    a light source configured to output low-coherence light;
    an optical coupler configured to generate the interference light by separating the low-coherence light into a signal light and a reference light and superimposing the signal light via the object to be measured on said reference light;
    an optical fiber configured to guide said interference light;
    a dispersion part configured to spectrally decompose said guided interference light;
    a detector configured to receive said spectrally decomposed interference light, an image forming part configured to form an image of the object to be measured by analyzing said interference light received by said detector;
    a specifying part configured to specify an amount of the interference light received on a light-receiving surface of said detector; and
    a drive mechanism configured to alter the relative position or orientation between said light-receiving surface and the exit end of said optical fiber, to the relative position or orientation when the amount of the received interference light reaches a substantial peak.

2. An optical image measuring device according to claim 1, wherein said drive mechanism comprises a driving part configured to generate a driving force and alter the position or direction of the exit end of said optical fiber with said driving force.

3. An optical image measuring device according to claim 1, wherein said drive mechanism comprises a driving part configured to generate a driving force and alters the position or direction of said light-receiving surface with said driving force.

4. An optical image measuring device according to claim 1, wherein said specifying part is configured to specify the amount of the received interference light about a plurality of arrangements between said light-receiving surface and the exit end, and said drive mechanism is configured to alter the relative position or orientation to the arrangement at the time of most amount of the received light among the specified plurality of received light amount.

5. An optical image measuring device according to claim 1, wherein said specifying part is configured to specify the irradiation position on said light-receiving surface when the amount of interference light received by said detector reaches a substantial peak, and said drive mechanism is configured to alter the relative position between said exit end and said light-receiving surface substantially to said specified irradiation position.

6. An optical image measuring device according to claim 5, wherein said specifying part preliminarily stores a peak value for the amount of light received by said detector and compares the amount of light received by said detector and said peak value to specify said irradiation position.

7. An optical image measuring device according to claim 5, wherein said specifying part preliminarily stores an allowable peak range for the amount of light received by said detector, and said drive mechanism alters the relative position between said exit end and said light-receiving surface only when the amount of light received by said detector is outside of said allowable peak range.

8. An optical image measuring device according to claim 5, wherein said specifying part preliminarily stores an allowable peak range for the amount of light received by said detector and further comprises a notifying part configured to output notifying information when said amount of the light received by said detector is not within said allowable peak range.

9. An optical image measuring device according to claim 1, wherein said specifying part is configured to analyze the amount of received light for each spectral component and specify the difference between the amounts of received light for respective spectral components to specify an irradiation orientation to said light-receiving surface, and said drive mechanism is configured to alter the relative direction of said exit end and said light-receiving surface based on said irradiation orientation.

10. An optical image measuring device according to claim 9, wherein said specifying part preliminarily stores an appropriate value of difference in the received light amount for each spectral component and compares said specified difference and said appropriate value to specify said irradiation direction.

11. An optical image measuring device according to claim 9, wherein said specifying part preliminarily stores an allowable range of difference in the received light amount for each spectral component, and said drive mechanism alters the relative direction between the exit end and said light-receiving surface only when said specified difference is outside of said allowable range.

12. An optical image measuring device according to claim 9, wherein said specifying part preliminarily stores an allowable range of difference in the amount of received light for each spectral component and further comprises a notifying part configured to output notifying information when said specified difference is outside of said allowable range.

13. An optical image measuring device according to claim 1, further comprising a prism member inserted into the light path between said exit end and said light-receiving surface by said drive mechanism.

* * * * *